United States Patent
Mathieu et al.

(10) Patent No.: US 10,492,922 B2
(45) Date of Patent: *Dec. 3, 2019

(54) INTERVERTEBRAL IMPLANT

(71) Applicant: DePuy Synthes Products, Inc., Raynham, MA (US)

(72) Inventors: Claude Mathieu, Zurich (CH); Christopher Marden John Cain, Aurora, CO (US)

(73) Assignee: DePuy Synthes Products, Inc., Raynham, MA (US)

( * ) Notice: Subject to any disclaimer, the term of this patent is extended or adjusted under 35 U.S.C. 154(b) by 32 days.

This patent is subject to a terminal disclaimer.

(21) Appl. No.: 15/401,713

(22) Filed: Jan. 9, 2017

(65) Prior Publication Data

US 2017/0143509 A1   May 25, 2017

Related U.S. Application Data

(63) Continuation of application No. 13/284,747, filed on Oct. 28, 2011, now Pat. No. 9,572,681, which is a
(Continued)

(51) Int. Cl.
*A61F 2/44* (2006.01)
*A61B 17/80* (2006.01)
(Continued)

(52) U.S. Cl.
CPC ........ *A61F 2/4465* (2013.01); *A61B 17/8052* (2013.01); *A61F 2/442* (2013.01);
(Continued)

(58) Field of Classification Search
None
See application file for complete search history.

(56) References Cited

U.S. PATENT DOCUMENTS

| 424,836 A | 4/1890 | Thompson |
| 438,892 A | 10/1890 | Lippy |

(Continued)

FOREIGN PATENT DOCUMENTS

| AU | 2004232317 A1 | 11/2004 |
| CA | 2111598 A1 | 6/1994 |

(Continued)

OTHER PUBLICATIONS

Polysciences Inc. Info Sheet 2012.
(Continued)

*Primary Examiner* — Bruce E Snow
(74) *Attorney, Agent, or Firm* — BakerHostetler

(57) ABSTRACT

The intervertebral implant is in the form of a three-dimensional structure (10) comprising (a) a top side (1) and an underside (2) which are designed to rest against the end plates of two adjacent vertebras, (b) a left side face (3) and a right side face (4), (c) a front face (5) and a rear face (6), (d) a horizontal center plane situated between the top side (1) and the underside (2), (e) a vertical center plane (8) situated between the left side face (3) and the right side face (8) and (f) a plurality of boreholes (9) passing through the implant structure (10) that are designed to receive longitudinal affixation elements (20), the axes (19) of said elements intersecting the horizontal center plane (7). At least one of the boreholes (9) is designed in a manner that the affixation element (10) received in it can be rigidly connected to the intervertebral implant. Said connection is implemented using a thread or by matching conical surfaces.

15 Claims, 3 Drawing Sheets

Related U.S. Application Data continuation of application No. 13/012,626, filed on Jan. 24, 2011, now abandoned, which is a continuation of application No. 12/574,222, filed on Oct. 6, 2009, now Pat. No. 7,875,076, which is a continuation of application No. 11/751,757, filed on May 22, 2007, now Pat. No. 7,618,456, which is a continuation of application No. 10/923,534, filed on Aug. 19, 2004, now Pat. No. 7,232,464, which is a continuation of application No. PCT/CH02/00099, filed on Feb. 19, 2002.

(51) Int. Cl.
  *A61B 17/86* (2006.01)
  *A61F 2/30* (2006.01)

(52) U.S. Cl.
  CPC ............ *A61F 2/447* (2013.01); *A61F 2/4455* (2013.01); *A61B 17/86* (2013.01); *A61F 2002/30004* (2013.01); *A61F 2002/30774* (2013.01); *A61F 2002/30777* (2013.01); *A61F 2002/30794* (2013.01); *A61F 2002/30841* (2013.01); *A61F 2002/4475* (2013.01); *A61F 2250/0014* (2013.01); *A61F 2310/00011* (2013.01)

(56) References Cited

U.S. PATENT DOCUMENTS

| | | |
|---|---|---|
| 1,105,105 A | 7/1914 | Sherman |
| 1,200,797 A | 10/1916 | Barbe |
| 2,151,919 A | 3/1939 | Jacobson |
| 2,372,888 A | 4/1945 | Duggan |
| 2,621,145 A | 12/1952 | Sano |
| 2,782,827 A | 2/1957 | Rosan |
| 2,906,311 A | 9/1959 | Boyd |
| 2,972,367 A | 2/1961 | Wootton |
| 3,062,253 A | 11/1962 | Millheiser |
| 3,272,249 A | 9/1966 | Houston |
| 3,350,103 A | 10/1967 | Ahlstone |
| 3,426,364 A | 2/1969 | Lumb |
| 3,561,075 A | 2/1971 | Selinko |
| 3,579,831 A | 5/1971 | Alexander |
| 3,707,303 A | 12/1972 | Petri |
| 3,810,703 A | 5/1974 | Pasbrig |
| 3,867,728 A | 2/1975 | Stubstad et al. |
| 3,899,897 A | 8/1975 | Boerger et al. |
| 3,945,671 A | 3/1976 | Gerlach |
| 4,017,946 A | 4/1977 | Soja |
| 4,056,301 A | 11/1977 | Norden |
| 4,123,132 A | 10/1978 | Hardy et al. |
| 4,135,506 A | 1/1979 | Ulrich |
| 4,278,120 A | 7/1981 | Hart et al. |
| 4,280,875 A | 7/1981 | Werres |
| 4,285,377 A | 8/1981 | Hart |
| 4,288,902 A | 9/1981 | Franz |
| 4,297,063 A | 10/1981 | Hart |
| 4,298,993 A | 11/1981 | Potekhin |
| 4,299,902 A | 11/1981 | Soma et al. |
| 4,349,921 A | 9/1982 | Kuntz |
| 4,388,921 A | 6/1983 | Sutter et al. |
| 4,394,370 A | 7/1983 | Jefferies |
| 4,450,591 A | 5/1984 | Rappaport |
| 4,484,570 A | 11/1984 | Sutter et al. |
| 4,488,543 A | 12/1984 | Tornier |
| 4,501,269 A | 2/1985 | Bagby |
| 4,503,848 A | 3/1985 | Caspar et al. |
| 4,512,038 A | 4/1985 | Alexander et al. |
| 4,545,374 A | 10/1985 | Jacobson |
| 4,553,890 A | 11/1985 | Gulistan |
| 4,599,086 A | 7/1986 | Doty |
| 4,627,853 A | 12/1986 | Campbell et al. |
| 4,640,524 A | 2/1987 | Sedlmair |
| 4,648,768 A | 3/1987 | Hambric |
| 4,678,470 A | 7/1987 | Nashef et al. |
| 4,708,377 A | 11/1987 | Hunting |
| 4,711,760 A | 12/1987 | Blaushild |
| 4,714,469 A | 12/1987 | Kenna |
| 4,717,115 A | 1/1988 | Schmitz et al. |
| 4,743,256 A | 5/1988 | Brantigan |
| 4,781,721 A | 11/1988 | Grundei |
| 4,793,335 A | 12/1988 | Frey et al. |
| 4,804,290 A | 2/1989 | Balsells |
| 4,812,094 A | 3/1989 | Grube |
| 4,829,152 A | 5/1989 | Rostoker |
| 4,834,757 A | 5/1989 | Brantigan |
| 4,858,603 A | 8/1989 | Clemow et al. |
| 4,872,452 A | 10/1989 | Alexson |
| 4,878,915 A | 11/1989 | Brantigan |
| 4,904,261 A | 2/1990 | Dove et al. |
| 4,917,704 A | 4/1990 | Frey et al. |
| 4,932,973 A | 6/1990 | Gendler |
| 4,936,851 A | 6/1990 | Fox et al. |
| 4,946,378 A | 8/1990 | Hirayama et al. |
| 4,950,296 A | 8/1990 | McIntyre |
| 4,955,908 A | 9/1990 | Frey et al. |
| 4,961,740 A | 10/1990 | Ray et al. |
| 4,976,576 A | 12/1990 | Mahaney, Jr. et al. |
| 4,978,350 A | 12/1990 | Wagenknecht |
| 4,994,084 A | 2/1991 | Brennan |
| 4,997,432 A | 3/1991 | Keller |
| 5,006,120 A | 4/1991 | Carter |
| 5,010,783 A | 4/1991 | Sparks et al. |
| 5,017,069 A | 5/1991 | Stencel |
| 5,020,949 A | 6/1991 | Davidson |
| 5,026,373 A | 6/1991 | Ray et al. |
| 5,030,220 A | 7/1991 | Howland |
| 5,047,058 A | 9/1991 | Roberts et al. |
| 5,053,049 A | 10/1991 | Campbell |
| 5,062,850 A | 11/1991 | MacMillan et al. |
| 5,071,437 A | 12/1991 | Steffee |
| 5,084,051 A | 1/1992 | Pellinen |
| 5,085,660 A | 2/1992 | Lin |
| 5,096,150 A | 3/1992 | Westwood |
| 5,108,438 A | 4/1992 | Stone |
| 5,112,354 A | 5/1992 | Sires |
| 5,116,374 A | 5/1992 | Stone |
| 5,118,235 A | 6/1992 | Dill |
| 5,139,424 A | 8/1992 | Yli-Urpo |
| 5,147,404 A | 9/1992 | Downey |
| 5,163,949 A | 11/1992 | Bonutti |
| 5,163,960 A | 11/1992 | Bonutti |
| 5,180,381 A | 1/1993 | Taylor |
| 5,192,327 A | 3/1993 | Brantigan |
| 5,197,971 A | 3/1993 | Bonutti |
| 5,201,736 A | 4/1993 | Strauss |
| 5,207,543 A | 5/1993 | Kirma |
| 5,211,664 A | 5/1993 | Tepic et al. |
| 5,235,034 A | 8/1993 | Bobsein et al. |
| 5,238,342 A | 8/1993 | Stencel |
| 5,258,031 A | 11/1993 | Salib et al. |
| 5,269,785 A | 12/1993 | Bonutti |
| 5,275,601 A | 1/1994 | Gogolewski et al. |
| 5,281,226 A | 1/1994 | Malakhov |
| 5,282,861 A | 2/1994 | Kaplan |
| 5,284,655 A | 2/1994 | Bogdansky et al. |
| 5,290,312 A | 3/1994 | Kojimoto et al. |
| 5,295,994 A | 3/1994 | Bonutti |
| 5,298,254 A | 3/1994 | Prewett et al. |
| 5,304,021 A | 4/1994 | Oliver et al. |
| 5,306,307 A | 4/1994 | Senter et al. |
| 5,306,308 A | 4/1994 | Gross et al. |
| 5,306,309 A | 4/1994 | Wagner et al. |
| 5,314,476 A | 5/1994 | Prewett et al. |
| 5,314,477 A | 5/1994 | Marnay |
| 5,329,846 A | 7/1994 | Bonutti |
| 5,330,535 A | 7/1994 | Moser et al. |
| 5,331,975 A | 7/1994 | Bonutti |
| 5,345,927 A | 9/1994 | Bonutti |
| 5,348,788 A | 9/1994 | White |
| 5,368,593 A | 11/1994 | Stark |
| 5,380,323 A | 1/1995 | Howland |

(56) References Cited

U.S. PATENT DOCUMENTS

| | | |
|---|---|---|
| 5,385,583 A | 1/1995 | Cotrel |
| 5,397,364 A | 3/1995 | Kozak et al. |
| 5,403,317 A | 4/1995 | Bonutti |
| 5,403,348 A | 4/1995 | Bonutti |
| 5,405,391 A | 4/1995 | Henderson et al. |
| 5,411,348 A | 5/1995 | Balsells |
| 5,423,817 A | 6/1995 | Lin |
| 5,425,772 A | 6/1995 | Brantigan |
| 5,431,658 A | 7/1995 | Moskovich |
| 5,439,684 A | 8/1995 | Prewett et al. |
| 5,441,538 A | 8/1995 | Bonutti |
| 5,443,514 A | 8/1995 | Steffee |
| 5,443,515 A | 8/1995 | Cohen et al. |
| 5,454,365 A | 10/1995 | Bonutti |
| 5,458,638 A | 10/1995 | Kuslich et al. |
| 5,458,641 A | 10/1995 | Ramirez Jimenez |
| 5,458,643 A | 10/1995 | Oka et al. |
| 5,464,426 A | 11/1995 | Bonutti |
| 5,478,342 A | 12/1995 | Kohrs |
| 5,484,437 A | 1/1996 | Michelson |
| 5,487,744 A | 1/1996 | Howland |
| 5,489,308 A | 2/1996 | Kuslich et al. |
| 5,496,348 A | 3/1996 | Bonutti |
| 5,507,818 A | 4/1996 | McLaughlin |
| 5,514,153 A | 5/1996 | Bonutti |
| 5,514,180 A | 5/1996 | Heggeness et al. |
| 5,520,690 A | 5/1996 | Errico et al. |
| 5,522,846 A | 6/1996 | Bonutti |
| 5,522,899 A | 6/1996 | Michelson |
| 5,527,343 A | 6/1996 | Bonutti |
| 5,531,746 A | 7/1996 | Errico et al. |
| 5,534,012 A | 7/1996 | Bonutti |
| 5,534,030 A | 7/1996 | Navarro et al. |
| 5,534,031 A | 7/1996 | Matsuzaki et al. |
| 5,534,032 A | 7/1996 | Hodorek |
| 5,545,222 A | 8/1996 | Bonutti |
| 5,545,842 A | 8/1996 | Balsells |
| 5,549,612 A | 8/1996 | Yapp et al. |
| 5,549,630 A | 8/1996 | Bonutti |
| 5,549,631 A | 8/1996 | Bonutti |
| 5,549,679 A | 8/1996 | Kuslich |
| 5,550,172 A | 8/1996 | Regula et al. |
| 5,554,191 A | 9/1996 | Lahille et al. |
| 5,556,430 A | 9/1996 | Gendler |
| 5,556,431 A | 9/1996 | Buttner-Janz |
| 5,569,305 A | 10/1996 | Bonutti |
| 5,569,308 A | 10/1996 | Sottosanti |
| 5,570,983 A | 11/1996 | Hollander |
| 5,571,109 A | 11/1996 | Bertagnoli |
| 5,571,190 A | 11/1996 | Ulrich |
| 5,571,192 A | 11/1996 | Schonhoffer |
| 5,577,517 A | 11/1996 | Bonutti |
| 5,578,034 A | 11/1996 | Estes |
| 5,584,862 A | 12/1996 | Bonutti |
| 5,593,409 A | 1/1997 | Michelson |
| 5,593,425 A | 1/1997 | Bonutti |
| 5,597,278 A | 1/1997 | Peterkort |
| 5,601,553 A | 2/1997 | Trebing et al. |
| 5,601,554 A | 2/1997 | Howland et al. |
| 5,607,428 A | 3/1997 | Lin |
| 5,607,474 A | 3/1997 | Athanasiou et al. |
| 5,609,635 A | 3/1997 | Michelson |
| 5,609,636 A | 3/1997 | Kohrs et al. |
| 5,609,637 A | 3/1997 | Biedermann et al. |
| 5,616,144 A | 4/1997 | Yapp et al. |
| 5,620,448 A | 4/1997 | Puddu |
| 5,624,462 A | 4/1997 | Bonutti |
| 5,642,960 A | 7/1997 | Salice |
| 5,645,596 A | 7/1997 | Kim et al. |
| 5,645,606 A | 7/1997 | Oehy et al. |
| 5,653,708 A | 8/1997 | Howland |
| 5,662,710 A | 9/1997 | Bonutti |
| 5,667,520 A | 9/1997 | Bonutti |
| 5,669,909 A | 9/1997 | Zdeblick et al. |
| 5,674,296 A | 10/1997 | Bryan et al. |
| 5,676,666 A | 10/1997 | Oxland et al. |
| 5,676,699 A | 10/1997 | Gogolewski et al. |
| 5,681,311 A | 10/1997 | Foley et al. |
| 5,683,216 A | 11/1997 | Erbes |
| 5,683,394 A | 11/1997 | Rinner |
| 5,683,463 A | 11/1997 | Godefroy et al. |
| 5,685,826 A | 11/1997 | Bonutti |
| 5,694,951 A | 12/1997 | Bonutti |
| 5,702,449 A | 12/1997 | McKay |
| 5,702,451 A | 12/1997 | Biedermann et al. |
| 5,702,453 A | 12/1997 | Rabbe et al. |
| 5,702,455 A | 12/1997 | Saggar |
| 5,707,390 A | 1/1998 | Bonutti |
| 5,713,899 A | 2/1998 | Marnay et al. |
| 5,713,900 A | 2/1998 | Benzel et al. |
| 5,716,325 A | 2/1998 | Bonutti |
| 5,725,531 A | 3/1998 | Shapiro |
| 5,725,588 A | 3/1998 | Errico et al. |
| 5,728,159 A | 3/1998 | Stroever et al. |
| 5,733,306 A | 3/1998 | Bonutti |
| 5,735,853 A | 4/1998 | Olerud |
| 5,735,875 A | 4/1998 | Bonutti |
| 5,735,905 A | 4/1998 | Parr |
| 5,755,796 A | 5/1998 | Ibo et al. |
| 5,755,798 A | 5/1998 | Papavero et al. |
| 5,766,251 A | 6/1998 | Koshino |
| 5,766,252 A | 6/1998 | Henry et al. |
| 5,766,253 A | 6/1998 | Brosnahan, III |
| 5,772,661 A | 6/1998 | Michelson |
| 5,776,194 A | 7/1998 | Mikol et al. |
| 5,776,196 A | 7/1998 | Matsuzaki et al. |
| 5,776,197 A | 7/1998 | Rabbe et al. |
| 5,776,198 A | 7/1998 | Rabbe et al. |
| 5,776,199 A | 7/1998 | Michelson |
| 5,778,804 A | 7/1998 | Read |
| 5,782,915 A | 7/1998 | Stone |
| 5,782,919 A | 7/1998 | Zdeblick et al. |
| 5,785,710 A | 7/1998 | Michelson |
| 5,800,433 A | 9/1998 | Benzel et al. |
| 5,827,318 A | 10/1998 | Bonutti |
| 5,836,948 A | 11/1998 | Zucherman et al. |
| 5,845,645 A | 12/1998 | Bonutti |
| 5,860,973 A | 1/1999 | Michelson |
| 5,860,997 A | 1/1999 | Bonutti |
| 5,861,041 A | 1/1999 | Tienboon |
| 5,865,845 A | 2/1999 | Thalgott |
| 5,865,849 A | 2/1999 | Stone |
| 5,872,915 A | 2/1999 | Dykes et al. |
| 5,876,402 A | 3/1999 | Errico et al. |
| 5,876,452 A | 3/1999 | Athanasiou et al. |
| 5,879,389 A | 3/1999 | Koshino |
| 5,885,299 A | 3/1999 | Winslow et al. |
| 5,888,196 A | 3/1999 | Bonutti |
| 5,888,219 A | 3/1999 | Bonutti |
| 5,888,222 A | 3/1999 | Coates et al. |
| 5,888,223 A | 3/1999 | Bray, Jr. |
| 5,888,224 A | 3/1999 | Beckers et al. |
| 5,888,227 A | 3/1999 | Cottle |
| 5,895,426 A | 4/1999 | Scarborough et al. |
| 5,899,939 A | 5/1999 | Boyce et al. |
| 5,902,303 A | 5/1999 | Eckhof et al. |
| 5,902,338 A | 5/1999 | Stone |
| 5,904,683 A | 5/1999 | Pohndorf et al. |
| 5,904,719 A | 5/1999 | Errico et al. |
| 5,906,616 A | 5/1999 | Pavlov et al. |
| 5,910,315 A | 6/1999 | Stevenson et al. |
| 5,911,758 A | 6/1999 | Oehy et al. |
| 5,920,312 A | 7/1999 | Wagner et al. |
| 5,922,027 A | 7/1999 | Stone |
| 5,928,267 A | 7/1999 | Bonutti |
| 5,931,838 A | 8/1999 | Vito |
| 5,935,131 A | 8/1999 | Bonutti |
| 5,941,900 A | 8/1999 | Bonutti |
| 5,944,755 A | 8/1999 | Stone |
| 5,951,558 A | 9/1999 | Fiz |
| 5,954,722 A | 9/1999 | Bono |
| 5,954,739 A | 9/1999 | Bonutti |
| 5,958,314 A | 9/1999 | Draenert |
| 5,964,807 A | 10/1999 | Gan et al. |

(56) References Cited

U.S. PATENT DOCUMENTS

| | | |
|---|---|---|
| 5,968,098 A | 10/1999 | Winslow |
| 5,972,031 A | 10/1999 | Biedermann |
| 5,972,368 A | 10/1999 | McKay |
| 5,976,141 A | 11/1999 | Haag et al. |
| 5,976,187 A | 11/1999 | Richelsoph |
| 5,980,522 A | 11/1999 | Koros et al. |
| 5,981,828 A | 11/1999 | Nelson et al. |
| 5,984,967 A | 11/1999 | Zdeblick et al. |
| 5,989,289 A | 11/1999 | Coates et al. |
| 6,001,099 A | 12/1999 | Huebner |
| 6,008,433 A | 12/1999 | Stone |
| 6,010,525 A | 1/2000 | Bonutti |
| 6,013,853 A | 1/2000 | Athanasiou et al. |
| 6,017,305 A | 1/2000 | Bonutti |
| 6,017,345 A | 1/2000 | Richelsoph |
| 6,025,538 A | 2/2000 | Yaccarino, III |
| 6,033,405 A | 3/2000 | Winslow et al. |
| 6,033,438 A | 3/2000 | Bianchi et al. |
| 6,039,762 A | 3/2000 | McKay |
| 6,042,596 A | 3/2000 | Bonutti |
| 6,045,579 A | 4/2000 | Hochshuler et al. |
| 6,045,580 A | 4/2000 | Scarborough et al. |
| 6,056,749 A | 5/2000 | Kuslich |
| 6,059,817 A | 5/2000 | Bonutti |
| 6,066,175 A | 5/2000 | Henderson et al. |
| 6,077,292 A | 6/2000 | Bonutti |
| 6,080,158 A | 6/2000 | Lin |
| 6,080,193 A | 6/2000 | Hochshuler et al. |
| 6,086,593 A | 7/2000 | Bonutti |
| 6,086,614 A | 7/2000 | Mumme |
| 6,090,998 A | 7/2000 | Grooms et al. |
| 6,096,080 A | 8/2000 | Nicholson et al. |
| 6,096,081 A | 8/2000 | Grivas et al. |
| 6,099,531 A | 8/2000 | Bonutti |
| 6,102,928 A | 8/2000 | Bonutti |
| 6,110,482 A | 8/2000 | Khouri et al. |
| 6,113,637 A | 9/2000 | Gill et al. |
| 6,113,638 A | 9/2000 | Williams et al. |
| 6,120,503 A | 9/2000 | Michelson |
| 6,123,731 A | 9/2000 | Boyce et al. |
| 6,129,763 A | 10/2000 | Chauvin et al. |
| 6,132,472 A | 10/2000 | Bonutti |
| 6,136,001 A | 10/2000 | Michelson |
| 6,139,550 A | 10/2000 | Michelson |
| RE36,974 E | 11/2000 | Bonutti |
| 6,143,030 A | 11/2000 | Schroder |
| 6,143,033 A | 11/2000 | Paul et al. |
| 6,146,421 A | 11/2000 | Gordon |
| 6,156,070 A | 12/2000 | Incavo et al. |
| 6,159,215 A | 12/2000 | Urbahns |
| 6,159,234 A | 12/2000 | Bonutti |
| 6,171,236 B1 | 1/2001 | Bonutti |
| 6,171,299 B1 | 1/2001 | Bonutti |
| 6,174,313 B1 | 1/2001 | Bonutti |
| 6,187,023 B1 | 2/2001 | Bonutti |
| 6,193,721 B1 | 2/2001 | Michelson |
| 6,193,756 B1 | 2/2001 | Studer et al. |
| 6,193,757 B1 | 2/2001 | Foley et al. |
| 6,200,347 B1 | 3/2001 | Anderson et al. |
| 6,203,565 B1 | 3/2001 | Bonutti et al. |
| 6,206,922 B1 | 3/2001 | Zdeblick et al. |
| 6,217,617 B1 | 4/2001 | Bonutti |
| 6,224,602 B1 | 5/2001 | Hayes |
| 6,231,592 B1 | 5/2001 | Bonutti et al. |
| 6,231,610 B1 | 5/2001 | Geisler |
| 6,235,033 B1 | 5/2001 | Brace et al. |
| 6,235,034 B1 | 5/2001 | Bray |
| 6,235,059 B1 | 5/2001 | Benezech et al. |
| 6,241,731 B1 | 6/2001 | Fiz |
| 6,241,769 B1 | 6/2001 | Nicholson et al. |
| 6,245,108 B1 | 6/2001 | Biscup |
| 6,258,089 B1 | 7/2001 | Campbell et al. |
| 6,258,125 B1 | 7/2001 | Paul et al. |
| 6,261,291 B1 | 7/2001 | Talaber et al. |
| 6,261,586 B1 | 7/2001 | McKay |
| 6,264,695 B1 | 7/2001 | Stoy |
| 6,270,528 B1 | 8/2001 | McKay |
| 6,277,136 B1 | 8/2001 | Bonutti |
| 6,287,325 B1 | 9/2001 | Bonutti |
| 6,306,139 B1 | 10/2001 | Fuentes |
| 6,322,562 B1 | 11/2001 | Wolter |
| 6,331,179 B1 | 12/2001 | Freid et al. |
| 6,342,074 B1 | 1/2002 | Simpson |
| 6,358,266 B1 | 3/2002 | Bonutti |
| 6,361,565 B1 | 3/2002 | Bonutti |
| 6,364,880 B1 | 4/2002 | Michelson |
| 6,368,343 B1 | 4/2002 | Bonutti |
| 6,371,986 B1 | 4/2002 | Bagby |
| 6,371,988 B1 | 4/2002 | Pafford et al. |
| 6,371,989 B1 | 4/2002 | Chauvin et al. |
| 6,375,681 B1 | 4/2002 | Truscott |
| 6,383,186 B1 | 5/2002 | Michelson |
| 6,387,130 B1 | 5/2002 | Stone et al. |
| 6,395,031 B1 | 5/2002 | Foley et al. |
| 6,398,811 B1 | 6/2002 | McKay |
| 6,413,259 B1 | 7/2002 | Lyons et al. |
| 6,423,063 B1 | 7/2002 | Bonutti |
| 6,432,106 B1 | 8/2002 | Fraser |
| 6,443,987 B1 | 9/2002 | Bryan |
| 6,447,512 B1 | 9/2002 | Landry et al. |
| 6,447,516 B1 | 9/2002 | Bonutti |
| 6,447,546 B1 | 9/2002 | Bramlet |
| 6,451,042 B1 | 9/2002 | Bonutti |
| 6,454,771 B1 | 9/2002 | Michelson |
| 6,458,158 B1 | 10/2002 | Anderson et al. |
| 6,461,359 B1 | 10/2002 | Tribus |
| 6,464,713 B2 | 10/2002 | Bonutti |
| 6,468,289 B1 | 10/2002 | Bonutti |
| 6,468,293 B2 | 10/2002 | Bonutti et al. |
| 6,468,311 B2 | 10/2002 | Boyd et al. |
| 6,471,724 B2 | 10/2002 | Zdeblick et al. |
| 6,475,230 B1 | 11/2002 | Bonutti |
| 6,482,233 B1 | 11/2002 | Aebi et al. |
| 6,500,195 B2 | 12/2002 | Bonutti |
| 6,503,250 B2 | 1/2003 | Paul |
| 6,503,267 B2 | 1/2003 | Bonutti et al. |
| 6,503,277 B2 | 1/2003 | Bonutti |
| 6,511,509 B1 | 1/2003 | Ford et al. |
| 6,524,312 B2 | 2/2003 | Landry et al. |
| 6,543,455 B2 | 4/2003 | Bonutti |
| 6,558,387 B2 | 5/2003 | Errico et al. |
| 6,558,423 B1 | 5/2003 | Michelson |
| 6,558,424 B2 | 5/2003 | Thalgott |
| 6,562,073 B2 | 5/2003 | Foley |
| 6,565,605 B2 | 5/2003 | Goble et al. |
| 6,569,187 B1 | 5/2003 | Bonutti |
| 6,569,201 B2 | 5/2003 | Moumene et al. |
| 6,575,975 B2 | 6/2003 | Brace et al. |
| 6,575,982 B1 | 6/2003 | Bonutti |
| 6,576,017 B2 | 6/2003 | Foley et al. |
| 6,579,290 B1 | 6/2003 | Hardcastle et al. |
| 6,585,750 B2 | 7/2003 | Bonutti et al. |
| 6,592,531 B2 | 7/2003 | Bonutti |
| 6,592,609 B1 | 7/2003 | Bonutti |
| 6,592,624 B1 | 7/2003 | Fraser et al. |
| 6,602,291 B1 | 8/2003 | Ray et al. |
| 6,605,090 B1 | 8/2003 | Trieu et al. |
| 6,607,534 B2 | 8/2003 | Bonutti |
| 6,616,671 B2 | 9/2003 | Landry et al. |
| 6,620,163 B1 | 9/2003 | Michelson |
| 6,620,181 B1 | 9/2003 | Bonutti |
| 6,623,486 B1 | 9/2003 | Weaver et al. |
| 6,629,998 B1 | 10/2003 | Lin |
| 6,630,000 B1 | 10/2003 | Bonutti |
| 6,635,073 B2 | 10/2003 | Bonutti |
| 6,638,309 B2 | 10/2003 | Bonutti |
| 6,638,310 B2 | 10/2003 | Lin et al. |
| 6,645,212 B2 | 11/2003 | Goldhahn et al. |
| 6,652,525 B1 | 11/2003 | Assaker et al. |
| 6,652,532 B2 | 11/2003 | Bonutti |
| 6,656,181 B2 | 12/2003 | Dixon et al. |
| 6,679,887 B2 | 1/2004 | Nicholson et al. |
| 6,682,561 B2 | 1/2004 | Songer et al. |
| 6,682,563 B2 | 1/2004 | Scharf |

(56) References Cited

U.S. PATENT DOCUMENTS

| | | |
|---|---|---|
| 6,695,846 B2 | 2/2004 | Richelsoph et al. |
| 6,695,851 B2 | 2/2004 | Zdeblick et al. |
| 6,702,821 B2 | 3/2004 | Bonutti |
| 6,702,856 B2 | 3/2004 | Bonutti |
| 6,706,067 B2 | 3/2004 | Shimp et al. |
| 6,709,456 B2 | 3/2004 | Langberg et al. |
| 6,712,818 B1 | 3/2004 | Michelson |
| 6,719,803 B2 | 4/2004 | Bonutti |
| 6,730,127 B2 | 5/2004 | Michelson |
| 6,736,850 B2 | 5/2004 | Davis |
| 6,736,853 B2 | 5/2004 | Bonutti |
| 6,743,257 B2 | 6/2004 | Castro |
| 6,761,738 B1 | 7/2004 | Boyd |
| 6,761,739 B2 | 7/2004 | Shepard |
| 6,770,078 B2 | 8/2004 | Bonutti |
| 6,770,096 B2 | 8/2004 | Bolger et al. |
| 6,776,938 B2 | 8/2004 | Bonutti |
| 6,786,909 B1 | 9/2004 | Dransfeld et al. |
| 6,800,092 B1 | 10/2004 | Williams et al. |
| 6,800,093 B2 | 10/2004 | Nicholson et al. |
| 6,805,714 B2 | 10/2004 | Sutcliffe |
| 6,808,537 B2 | 10/2004 | Michelson |
| 6,824,564 B2 | 11/2004 | Crozet |
| 6,833,006 B2 | 12/2004 | Foley et al. |
| 6,835,198 B2 | 12/2004 | Bonutti |
| 6,837,905 B1 | 1/2005 | Lieberman |
| 6,849,093 B2 | 2/2005 | Michelson |
| 6,855,167 B2 | 2/2005 | Shimp et al. |
| 6,855,168 B2 | 2/2005 | Crozet |
| 6,860,885 B2 | 3/2005 | Bonutti |
| 6,860,904 B2 | 3/2005 | Bonutti |
| 6,863,673 B2 | 3/2005 | Gerbec et al. |
| 6,872,915 B2 | 3/2005 | Koga et al. |
| 6,884,242 B2 | 4/2005 | LeHuec et al. |
| 6,890,334 B2 | 5/2005 | Brace et al. |
| 6,896,701 B2 | 5/2005 | Boyd et al. |
| 6,899,735 B2 | 5/2005 | Coates et al. |
| 6,902,578 B1 | 6/2005 | Anderson et al. |
| 6,905,517 B2 | 6/2005 | Bonutti |
| 6,908,466 B1 | 6/2005 | Bonutti et al. |
| 6,916,320 B2 | 7/2005 | Michelson |
| 6,923,756 B2 | 8/2005 | Sudakov et al. |
| 6,932,835 B2 | 8/2005 | Bonutti et al. |
| 6,953,477 B2 | 10/2005 | Berry |
| 6,962,606 B2 | 11/2005 | Michelson |
| 6,964,664 B2 | 11/2005 | Freid et al. |
| 6,964,687 B1 | 11/2005 | Bernard et al. |
| 6,972,019 B2 | 12/2005 | Michelson |
| 6,972,035 B2 | 12/2005 | Michelson |
| 6,974,479 B2 | 12/2005 | Trieu |
| 6,984,234 B2 | 1/2006 | Bray |
| 6,989,029 B2 | 1/2006 | Bonutti |
| 6,990,982 B1 | 1/2006 | Bonutti |
| 7,001,385 B2 | 2/2006 | Bonutti |
| 7,001,432 B2 | 2/2006 | Keller et al. |
| 7,018,412 B2 | 3/2006 | Ferreira et al. |
| 7,018,416 B2 | 3/2006 | Hanson et al. |
| 7,033,394 B2 | 4/2006 | Michelson |
| 7,041,135 B2 | 5/2006 | Michelson |
| 7,044,968 B1 | 5/2006 | Yaccarino, III et al. |
| 7,044,972 B2 | 5/2006 | Mathys, Jr. et al. |
| 7,048,755 B2 | 5/2006 | Bonutti et al. |
| 7,048,765 B1 | 5/2006 | Grooms et al. |
| 7,060,097 B2 | 6/2006 | Fraser et al. |
| 7,066,961 B2 | 6/2006 | Michelson |
| 7,070,557 B2 | 7/2006 | Bonutti |
| 7,077,864 B2 | 7/2006 | Byrd, III et al. |
| 7,087,073 B2 | 8/2006 | Bonutti |
| 7,094,251 B2 | 8/2006 | Bonutti et al. |
| 7,104,996 B2 | 9/2006 | Bonutti |
| 7,112,222 B2 | 9/2006 | Fraser et al. |
| 7,112,223 B2 | 9/2006 | Davis |
| 7,114,500 B2 | 10/2006 | Bonutti |
| 7,128,753 B1 | 10/2006 | Bonutti et al. |
| 7,134,437 B2 | 11/2006 | Bonutti |
| 7,135,024 B2 | 11/2006 | Cook et al. |
| 7,135,043 B2 | 11/2006 | Nakahara et al. |
| 7,137,984 B2 | 11/2006 | Michelson |
| 7,147,652 B2 | 12/2006 | Bonutti |
| 7,147,665 B1 | 12/2006 | Bryan et al. |
| 7,163,561 B2 | 1/2007 | Michelson |
| 7,172,627 B2 | 2/2007 | Fiere et al. |
| 7,172,672 B2 | 2/2007 | Silverbrook |
| 7,208,013 B1 | 4/2007 | Bonutti |
| 7,217,273 B2 | 5/2007 | Bonutti |
| 7,217,290 B2 | 5/2007 | Bonutti |
| 7,226,452 B2 | 6/2007 | Zubok et al. |
| 7,226,482 B2 | 6/2007 | Messerli et al. |
| 7,232,463 B2 | 6/2007 | Falahee |
| 7,232,464 B2 * | 6/2007 | Mathieu ............ A61B 17/8052 623/17.11 |
| 7,238,203 B2 | 7/2007 | Bagga et al. |
| 7,255,698 B2 | 8/2007 | Michelson |
| 7,276,082 B2 | 10/2007 | Zdeblick et al. |
| 7,311,719 B2 | 12/2007 | Bonutti |
| 7,320,708 B1 | 1/2008 | Bernstein |
| 7,323,011 B2 | 1/2008 | Shepard et al. |
| 7,329,263 B2 | 2/2008 | Bonutti et al. |
| 7,398,623 B2 | 7/2008 | Martel et al. |
| 7,429,266 B2 | 9/2008 | Bonutti et al. |
| 7,442,209 B2 | 10/2008 | Michelson |
| 7,462,200 B2 | 12/2008 | Bonutti |
| 7,481,831 B2 | 1/2009 | Bonutti |
| 7,485,145 B2 | 2/2009 | Purcell |
| 7,491,237 B2 | 2/2009 | Randall et al. |
| 7,510,557 B1 | 3/2009 | Bonutti |
| 7,534,265 B1 | 5/2009 | Boyd et al. |
| 7,594,932 B2 | 9/2009 | Aferzon et al. |
| 7,601,173 B2 | 10/2009 | Messerli et al. |
| 7,608,107 B2 | 10/2009 | Michelson |
| 7,615,054 B1 | 11/2009 | Bonutti |
| 7,618,456 B2 * | 11/2009 | Mathieu ............ A61B 17/8052 623/17.11 |
| 7,621,960 B2 | 11/2009 | Boyd et al. |
| 7,625,380 B2 | 12/2009 | Drewry et al. |
| 7,635,390 B1 | 12/2009 | Bonutti |
| 7,637,951 B2 | 12/2009 | Michelson |
| 7,655,042 B2 | 2/2010 | Foley et al. |
| 7,704,279 B2 | 4/2010 | Moskowitz et al. |
| 7,708,740 B1 | 5/2010 | Bonutti |
| 7,708,741 B1 | 5/2010 | Bonutti |
| 7,727,283 B2 | 6/2010 | Bonutti |
| 7,749,229 B1 | 7/2010 | Bonutti |
| 7,776,067 B2 | 8/2010 | Jackson |
| 7,780,670 B2 | 8/2010 | Bonutti |
| 7,806,896 B1 | 10/2010 | Bonutti |
| 7,806,897 B1 | 10/2010 | Bonutti |
| 7,828,852 B2 | 11/2010 | Bonutti |
| 7,833,271 B2 | 11/2010 | Mitchell et al. |
| 7,837,736 B2 | 11/2010 | Bonutti |
| 7,846,188 B2 | 12/2010 | Moskowitz et al. |
| 7,846,207 B2 | 12/2010 | Lechmann et al. |
| 7,854,750 B2 | 12/2010 | Bonutti et al. |
| 7,862,616 B2 | 1/2011 | Lechmann et al. |
| 7,875,076 B2 * | 1/2011 | Mathieu ............ A61B 17/8052 623/17.11 |
| 7,879,072 B2 | 2/2011 | Bonutti et al. |
| 7,892,236 B1 | 2/2011 | Bonutti |
| 7,892,261 B2 | 2/2011 | Bonutti |
| 7,896,880 B2 | 3/2011 | Bonutti |
| 7,931,690 B1 | 4/2011 | Bonutti |
| 7,942,903 B2 | 5/2011 | Moskowitz et al. |
| 7,959,635 B1 | 6/2011 | Bonutti |
| 7,985,255 B2 | 7/2011 | Bray et al. |
| 7,993,403 B2 | 8/2011 | Foley et al. |
| 8,062,303 B2 | 11/2011 | Berry et al. |
| 8,100,976 B2 | 1/2012 | Bray et al. |
| 8,105,383 B2 | 1/2012 | Michelson |
| 8,128,669 B2 | 3/2012 | Bonutti |
| 8,128,700 B2 | 3/2012 | Delurio et al. |
| 8,133,229 B1 | 3/2012 | Bonutti |
| 8,162,977 B2 | 4/2012 | Bonutti et al. |
| 8,182,532 B2 | 5/2012 | Anderson et al. |
| 8,187,329 B2 | 5/2012 | Theofilos |

(56) References Cited

U.S. PATENT DOCUMENTS

| | | |
|---|---|---|
| 8,211,148 B2 | 7/2012 | Zhang et al. |
| 8,273,127 B2 | 9/2012 | Jones et al. |
| 8,308,804 B2 | 11/2012 | Krueger |
| 8,328,872 B2 | 12/2012 | Duffield et al. |
| 8,343,220 B2 | 1/2013 | Michelson |
| 8,343,222 B2 | 1/2013 | Cope |
| 8,353,913 B2 | 1/2013 | Alvarado |
| 8,382,768 B2 | 2/2013 | Lee |
| 8,425,522 B2 | 4/2013 | Bonutti |
| 8,425,607 B2 | 4/2013 | Waugh et al. |
| 8,444,696 B2 | 5/2013 | Michelson |
| 8,465,546 B2 | 6/2013 | Jodaitis et al. |
| 8,486,066 B2 | 7/2013 | Bonutti |
| 8,540,774 B2 | 9/2013 | Kueenzi et al. |
| 8,545,567 B1 | 10/2013 | Krueger |
| 8,613,772 B2 | 12/2013 | Bray et al. |
| 8,623,030 B2 | 1/2014 | Bonutti |
| 8,632,552 B2 | 1/2014 | Bonutti |
| 8,641,726 B2 | 2/2014 | Bonutti |
| 8,641,743 B2 | 2/2014 | Michelson |
| 8,641,768 B2 | 2/2014 | Duffield et al. |
| 8,690,944 B2 | 4/2014 | Bonutti |
| 8,739,797 B2 | 6/2014 | Bonutti |
| 8,747,439 B2 | 6/2014 | Bonutti et al. |
| 8,764,831 B2 | 7/2014 | Lechmann et al. |
| 8,784,495 B2 | 7/2014 | Bonutti |
| 8,795,363 B2 | 8/2014 | Bonutti |
| 8,814,902 B2 | 8/2014 | Bonutti |
| 8,834,490 B2 | 9/2014 | Bonutti |
| 8,840,629 B2 | 9/2014 | Bonutti |
| 8,845,699 B2 | 9/2014 | Bonutti |
| 8,858,557 B2 | 10/2014 | Bonutti |
| 8,956,417 B2 | 2/2015 | Bonutti |
| 9,005,295 B2 | 4/2015 | Kueenzi et al. |
| 9,044,322 B2 | 6/2015 | Bonutti |
| 9,044,341 B2 | 6/2015 | Bonutti |
| 9,050,152 B2 | 6/2015 | Bonutti |
| 9,149,365 B2 | 10/2015 | Lawson et al. |
| 9,220,604 B2 | 12/2015 | McDonough et al. |
| 9,241,809 B2 | 1/2016 | McDonough et al. |
| 9,364,340 B2 | 6/2016 | Lawson et al. |
| 9,414,935 B2 | 8/2016 | McDonough et al. |
| 9,463,097 B2 | 10/2016 | Lechmann et al. |
| 9,572,681 B2 * | 2/2017 | Mathieu ............ A61B 17/8052 |
| 9,744,049 B2 | 8/2017 | Kueenzi et al. |
| 9,848,992 B2 | 12/2017 | McDonough et al. |
| 9,883,950 B2 | 2/2018 | Bertagnoli et al. |
| 2001/0001129 A1 | 5/2001 | McKay et al. |
| 2001/0005796 A1 | 6/2001 | Zdeblick et al. |
| 2001/0010021 A1 | 7/2001 | Boyd et al. |
| 2001/0016777 A1 | 8/2001 | Biscup |
| 2001/0020186 A1 | 9/2001 | Boyce et al. |
| 2001/0023371 A1 | 9/2001 | Bonutti |
| 2001/0031254 A1 | 10/2001 | Bianchi et al. |
| 2001/0039456 A1 | 11/2001 | Boyer et al. |
| 2001/0041941 A1 | 11/2001 | Boyer et al. |
| 2001/0049560 A1 | 12/2001 | Paul et al. |
| 2002/0004683 A1 | 1/2002 | Michelson |
| 2002/0010511 A1 | 1/2002 | Michelson |
| 2002/0016595 A1 | 2/2002 | Michelson |
| 2002/0022843 A1 | 2/2002 | Michelson |
| 2002/0029055 A1 | 3/2002 | Bonutti |
| 2002/0029084 A1 | 3/2002 | Paul et al. |
| 2002/0040246 A1 | 4/2002 | Bonutti |
| 2002/0049497 A1 | 4/2002 | Mason |
| 2002/0065517 A1 | 5/2002 | Paul |
| 2002/0082597 A1 | 6/2002 | Fraser |
| 2002/0082603 A1 | 6/2002 | Dixon et al. |
| 2002/0082803 A1 | 6/2002 | Schiffbauer |
| 2002/0091447 A1 | 7/2002 | Shimp et al. |
| 2002/0095155 A1 | 7/2002 | Michelson |
| 2002/0095160 A1 | 7/2002 | Bonutti |
| 2002/0099376 A1 | 7/2002 | Michelson |
| 2002/0099378 A1 | 7/2002 | Michelson |
| 2002/0099444 A1 | 7/2002 | Boyd et al. |
| 2002/0106393 A1 | 8/2002 | Bianchi et al. |
| 2002/0107571 A1 | 8/2002 | Foley |
| 2002/0111680 A1 | 8/2002 | Michelson |
| 2002/0128712 A1 | 9/2002 | Michelson |
| 2002/0128717 A1 | 9/2002 | Alfaro et al. |
| 2002/0147450 A1 | 10/2002 | Lehuec et al. |
| 2002/0161444 A1 | 10/2002 | Choi |
| 2002/0169508 A1 | 11/2002 | Songer et al. |
| 2002/0193880 A1 | 12/2002 | Fraser |
| 2003/0004576 A1 | 1/2003 | Thalgott |
| 2003/0009147 A1 | 1/2003 | Bonutti |
| 2003/0023260 A1 | 1/2003 | Bonutti |
| 2003/0045939 A1 | 3/2003 | Casutt |
| 2003/0078666 A1 | 4/2003 | Ralph et al. |
| 2003/0078668 A1 | 4/2003 | Michelson |
| 2003/0125739 A1 | 7/2003 | Bagga et al. |
| 2003/0135277 A1 | 7/2003 | Bryan et al. |
| 2003/0153975 A1 | 8/2003 | Byrd et al. |
| 2003/0167092 A1 | 9/2003 | Foley |
| 2003/0181981 A1 | 9/2003 | Lemaire |
| 2003/0195626 A1 | 10/2003 | Huppert |
| 2003/0195632 A1 | 10/2003 | Foley et al. |
| 2003/0199881 A1 | 10/2003 | Bonutti |
| 2003/0199983 A1 | 10/2003 | Michelson |
| 2004/0010287 A1 | 1/2004 | Bonutti |
| 2004/0078078 A1 | 4/2004 | Shepard |
| 2004/0078081 A1 | 4/2004 | Ferree |
| 2004/0092929 A1 | 5/2004 | Zindrick |
| 2004/0093084 A1 | 5/2004 | Michelson |
| 2004/0097794 A1 | 5/2004 | Bonutti |
| 2004/0098016 A1 | 5/2004 | Bonutti |
| 2004/0102848 A1 | 5/2004 | Michelson |
| 2004/0102850 A1 | 5/2004 | Shepard |
| 2004/0126407 A1 | 7/2004 | Falahee |
| 2004/0133278 A1 | 7/2004 | Marino et al. |
| 2004/0138689 A1 | 7/2004 | Bonutti |
| 2004/0138690 A1 | 7/2004 | Bonutti |
| 2004/0143270 A1 | 7/2004 | Zucherman et al. |
| 2004/0143285 A1 | 7/2004 | Bonutti |
| 2004/0172033 A1 | 9/2004 | Bonutti |
| 2004/0176853 A1 | 9/2004 | Sennett et al. |
| 2004/0193181 A1 | 9/2004 | Bonutti |
| 2004/0193269 A1 | 9/2004 | Fraser et al. |
| 2004/0199254 A1 | 10/2004 | Louis et al. |
| 2004/0210219 A1 | 10/2004 | Bray |
| 2004/0210310 A1 | 10/2004 | Trieu |
| 2004/0210314 A1 | 10/2004 | Michelson |
| 2004/0220668 A1 | 11/2004 | Eisermann et al. |
| 2004/0230223 A1 | 11/2004 | Bonutti et al. |
| 2004/0249377 A1 | 12/2004 | Kaes et al. |
| 2004/0254644 A1 | 12/2004 | Taylor |
| 2004/0260427 A1 | 12/2004 | Wimsatt |
| 2005/0015149 A1 | 1/2005 | Michelson |
| 2005/0021042 A1 | 1/2005 | Marnay et al. |
| 2005/0021143 A1 | 1/2005 | Keller |
| 2005/0033433 A1 | 2/2005 | Michelson |
| 2005/0049593 A1 | 3/2005 | Duong et al. |
| 2005/0049595 A1 | 3/2005 | Suh et al. |
| 2005/0065605 A1 | 3/2005 | Jackson |
| 2005/0065607 A1 | 3/2005 | Gross |
| 2005/0065608 A1 | 3/2005 | Michelson |
| 2005/0071008 A1 | 3/2005 | Kirschman |
| 2005/0085913 A1 | 4/2005 | Fraser et al. |
| 2005/0101960 A1 | 5/2005 | Fiere et al. |
| 2005/0113918 A1 | 5/2005 | Messerli et al. |
| 2005/0113920 A1 | 5/2005 | Foley et al. |
| 2005/0125029 A1 | 6/2005 | Bernard et al. |
| 2005/0149193 A1 | 7/2005 | Zucherman et al. |
| 2005/0154391 A1 | 7/2005 | Doherty et al. |
| 2005/0159813 A1 | 7/2005 | Molz, IV |
| 2005/0159818 A1 | 7/2005 | Blain |
| 2005/0159819 A1 | 7/2005 | McCormack et al. |
| 2005/0171606 A1 | 8/2005 | Michelson |
| 2005/0171607 A1 | 8/2005 | Michelson |
| 2005/0177236 A1 | 8/2005 | Mathieu et al. |
| 2005/0216059 A1 | 9/2005 | Bonutti et al. |
| 2005/0222683 A1 | 10/2005 | Berry |
| 2005/0240267 A1 | 10/2005 | Randall et al. |
| 2005/0240271 A1 | 10/2005 | Zubok et al. |

(56) References Cited

U.S. PATENT DOCUMENTS

| | | |
|---|---|---|
| 2005/0261767 A1 | 11/2005 | Anderson et al. |
| 2005/0267534 A1 | 12/2005 | Bonutti et al. |
| 2006/0020342 A1 | 1/2006 | Ferree et al. |
| 2006/0030851 A1 | 2/2006 | Bray et al. |
| 2006/0079901 A1 | 4/2006 | Ryan et al. |
| 2006/0079961 A1 | 4/2006 | Michelson |
| 2006/0085071 A1 | 4/2006 | Lechmann et al. |
| 2006/0089717 A1 | 4/2006 | Krishna et al. |
| 2006/0129240 A1 | 6/2006 | Lessar et al. |
| 2006/0136063 A1 | 6/2006 | Zeegers |
| 2006/0142765 A9 | 6/2006 | Dixon et al. |
| 2006/0167495 A1 | 7/2006 | Bonutti et al. |
| 2006/0195189 A1 | 8/2006 | Link et al. |
| 2006/0195193 A1 | 8/2006 | Bloemer |
| 2006/0206208 A1 | 9/2006 | Michelson |
| 2006/0229725 A1 | 10/2006 | Lechmann et al. |
| 2006/0235470 A1 | 10/2006 | Bonutti et al. |
| 2006/0265009 A1 | 11/2006 | Bonutti |
| 2007/0088358 A1 | 4/2007 | Yuan et al. |
| 2007/0088441 A1 | 4/2007 | Duggal et al. |
| 2007/0093819 A1 | 4/2007 | Albert |
| 2007/0106384 A1 | 5/2007 | Bray et al. |
| 2007/0118125 A1 | 5/2007 | Orbay et al. |
| 2007/0123987 A1 | 5/2007 | Bernstein |
| 2007/0162130 A1 | 7/2007 | Rashbaum et al. |
| 2007/0168032 A1 | 7/2007 | Muhanna |
| 2007/0177236 A1 | 8/2007 | Kijima et al. |
| 2007/0208378 A1 | 9/2007 | Bonutti et al. |
| 2007/0219365 A1 | 9/2007 | Joyce et al. |
| 2007/0219635 A1 | 9/2007 | Mathieu et al. |
| 2007/0225806 A1 | 9/2007 | Squires et al. |
| 2007/0225812 A1 | 9/2007 | Gill |
| 2007/0250167 A1 | 10/2007 | Bray et al. |
| 2007/0270961 A1 | 11/2007 | Ferguson |
| 2008/0033440 A1 | 2/2008 | Moskowitz et al. |
| 2008/0039873 A1 | 2/2008 | Bonutti et al. |
| 2008/0047567 A1 | 2/2008 | Bonutti |
| 2008/0051890 A1 | 2/2008 | Waugh et al. |
| 2008/0058822 A1 | 3/2008 | Bonutti |
| 2008/0065140 A1 | 3/2008 | Bonutti |
| 2008/0082169 A1 | 4/2008 | Gittings et al. |
| 2008/0103519 A1 | 5/2008 | Bonutti |
| 2008/0108916 A1 | 5/2008 | Bonutti et al. |
| 2008/0114399 A1 | 5/2008 | Bonutti |
| 2008/0119933 A1 | 5/2008 | Aebi et al. |
| 2008/0132949 A1 | 6/2008 | Aferzon et al. |
| 2008/0133013 A1 | 6/2008 | Duggal et al. |
| 2008/0140116 A1 | 6/2008 | Bonutti |
| 2008/0140117 A1 | 6/2008 | Bonutti et al. |
| 2008/0161925 A1 | 7/2008 | Brittan et al. |
| 2008/0177307 A1 | 7/2008 | Moskowitz et al. |
| 2008/0188940 A1 | 8/2008 | Cohen et al. |
| 2008/0200984 A1 | 8/2008 | Jodaitis et al. |
| 2008/0234822 A1 | 9/2008 | Govil et al. |
| 2008/0249569 A1 | 10/2008 | Waugh et al. |
| 2008/0249575 A1 | 10/2008 | Waugh et al. |
| 2008/0249622 A1 | 10/2008 | Gray |
| 2008/0249625 A1 | 10/2008 | Waugh et al. |
| 2008/0269806 A1 | 10/2008 | Zhang et al. |
| 2008/0275455 A1 | 11/2008 | Berry et al. |
| 2008/0281425 A1 | 11/2008 | Thalgott et al. |
| 2008/0306596 A1 | 12/2008 | Jones et al. |
| 2008/0312742 A1 | 12/2008 | Abernathie |
| 2009/0076608 A1 | 3/2009 | Gordon et al. |
| 2009/0088849 A1 | 4/2009 | Armstrong et al. |
| 2009/0099661 A1 | 4/2009 | Bhattacharya et al. |
| 2009/0105830 A1 | 4/2009 | Jones et al. |
| 2009/0132051 A1 | 5/2009 | Moskowitz et al. |
| 2009/0192613 A1 | 7/2009 | Wing et al. |
| 2009/0210062 A1 | 8/2009 | Thalgott et al. |
| 2009/0210064 A1 | 8/2009 | Lechmann et al. |
| 2009/0234455 A1 | 9/2009 | Moskowitz et al. |
| 2009/0326580 A1 | 12/2009 | Anderson et al. |
| 2010/0016901 A1 | 1/2010 | Robinson |
| 2010/0125334 A1 | 5/2010 | Krueger |
| 2010/0145459 A1 | 6/2010 | McDonough et al. |
| 2010/0145460 A1 | 6/2010 | McDonough et al. |
| 2010/0305704 A1 | 12/2010 | Messerli et al. |
| 2010/0312346 A1 | 12/2010 | Kueenzi et al. |
| 2011/0087327 A1 | 4/2011 | Lechmann et al. |
| 2011/0118843 A1 | 5/2011 | Mathieu et al. |
| 2011/0137417 A1 | 6/2011 | Lee |
| 2011/0166660 A1 | 7/2011 | Laurence |
| 2011/0230971 A1 | 9/2011 | Donner et al. |
| 2011/0238184 A1 | 9/2011 | Zdeblick et al. |
| 2011/0295371 A1 | 12/2011 | Moskowitz |
| 2012/0010623 A1 | 1/2012 | Bonutti |
| 2012/0101581 A1 | 4/2012 | Cain |
| 2012/0109309 A1 | 5/2012 | Cain |
| 2012/0109310 A1 | 5/2012 | Cain |
| 2012/0109311 A1 | 5/2012 | Cain |
| 2012/0109312 A1 | 5/2012 | Cain |
| 2012/0109313 A1 | 5/2012 | Cain |
| 2012/0179259 A1 | 7/2012 | Schmura |
| 2012/0197401 A1 | 8/2012 | Duncan et al. |
| 2012/0215226 A1 | 8/2012 | Bonutti |
| 2012/0215233 A1 | 8/2012 | Cremens |
| 2012/0221017 A1 | 8/2012 | Bonutti |
| 2012/0323330 A1 | 12/2012 | Kueenzi et al. |
| 2013/0073046 A1 | 3/2013 | Seifert |
| 2013/0073047 A1 | 3/2013 | Boyer, II et al. |
| 2013/0166032 A1 | 6/2013 | Schmura |
| 2013/0173013 A1 | 7/2013 | Anderson et al. |
| 2013/0226185 A1 | 8/2013 | Bonutti |
| 2013/0237989 A1 | 9/2013 | Bonutti |
| 2013/0268008 A1 | 10/2013 | Berger |
| 2013/0289729 A1 | 10/2013 | Bonutti |
| 2014/0018854 A1 | 1/2014 | Bonutti et al. |
| 2014/0025110 A1 | 1/2014 | Bonutti et al. |
| 2014/0025111 A1 | 1/2014 | Bonutti |
| 2014/0025112 A1 | 1/2014 | Bonutti |
| 2014/0025168 A1 | 1/2014 | Laskowitz |
| 2014/0100663 A1 | 4/2014 | Messerli et al. |
| 2014/0121777 A1 | 5/2014 | Laskowitz |
| 2014/0180422 A1 | 6/2014 | Klimek et al. |
| 2014/0214166 A1 | 7/2014 | Theofilos |
| 2014/0228963 A1 | 8/2014 | Bonutti |
| 2014/0243985 A1 | 8/2014 | Lechmann et al. |
| 2014/0257380 A1 | 9/2014 | Bonutti |
| 2014/0257487 A1 | 9/2014 | Lawson et al. |
| 2014/0277456 A1 | 9/2014 | Kirschman |
| 2014/0309560 A1 | 10/2014 | Bonutti |
| 2014/0336770 A1 | 11/2014 | Petersheim et al. |
| 2014/0343573 A1 | 11/2014 | Bonutti |
| 2014/0371859 A1 | 12/2014 | Petersheim et al. |
| 2015/0257893 A1 | 9/2015 | Gamache |
| 2015/0320571 A1 | 11/2015 | Lechmann et al. |
| 2016/0113774 A1 | 4/2016 | Schmura et al. |

FOREIGN PATENT DOCUMENTS

| | | |
|---|---|---|
| CA | 2317791 A1 | 8/1999 |
| CN | 1383790 A | 12/2002 |
| CN | 1620271 A | 5/2005 |
| CN | 1701772 A | 11/2005 |
| CN | 1901853 A | 1/2007 |
| DE | 2821678 A | 11/1979 |
| DE | 3042003 A1 | 7/1982 |
| DE | 3933459 A1 | 4/1991 |
| DE | 4242889 A1 | 6/1994 |
| DE | 4409392 A1 | 9/1995 |
| DE | 4423257 A1 | 1/1996 |
| DE | 19504867 C1 | 2/1996 |
| DE | 29913200 U1 | 9/1999 |
| DE | 202004020209 U1 | 5/2006 |
| EP | 0179695 A1 | 4/1986 |
| EP | 0302719 A1 | 2/1989 |
| EP | 0505634 A1 | 9/1992 |
| EP | 0577178 A1 | 1/1994 |
| EP | 0639351 A2 | 2/1995 |
| EP | 0425542 B1 | 3/1995 |
| EP | 0504346 B1 | 5/1995 |
| EP | 0517030 B1 | 9/1996 |
| EP | 0897697 A1 | 2/1999 |

(56) References Cited

FOREIGN PATENT DOCUMENTS

| | | |
|---|---|---|
| EP | 0605799 B1 | 4/1999 |
| EP | 0641547 B1 | 5/1999 |
| EP | 0966930 A1 | 12/1999 |
| EP | 0968692 A1 | 1/2000 |
| EP | 0974319 A2 | 1/2000 |
| EP | 1124512 A1 | 8/2001 |
| EP | 1194087 A1 | 4/2002 |
| EP | 1393689 A2 | 3/2004 |
| EP | 1402836 A2 | 3/2004 |
| EP | 1033941 B1 | 8/2004 |
| EP | 0906065 B1 | 9/2004 |
| EP | 1051133 B1 | 10/2004 |
| EP | 1103236 B1 | 8/2006 |
| EP | 1459711 B1 | 7/2007 |
| EP | 1847240 A1 | 10/2007 |
| FR | 2552659 A3 | 4/1985 |
| FR | 2697996 A1 | 5/1994 |
| FR | 2700947 A1 | 8/1994 |
| FR | 2703580 A1 | 10/1994 |
| FR | 2727003 A1 | 5/1996 |
| FR | 2747034 A1 | 10/1997 |
| FR | 2753368 A1 | 3/1998 |
| GB | 0157668 A | 1/1921 |
| GB | 0265592 A | 8/1927 |
| GB | 2148122 A | 5/1985 |
| GB | 2207607 A | 2/1989 |
| GB | 2239482 A | 7/1991 |
| GB | 2266246 A | 10/1993 |
| JP | 03-505416 A | 11/1991 |
| JP | 09-280219 A | 10/1997 |
| JP | 2006-513752 A | 4/2006 |
| RU | 2229271 C1 | 5/2004 |
| RU | 2244527 C2 | 1/2005 |
| RU | 2307625 C1 | 10/2007 |
| SU | 1465040 A1 | 3/1989 |
| WO | 88/03417 A1 | 5/1988 |
| WO | 88/10100 A1 | 12/1988 |
| WO | 89/09035 A1 | 10/1989 |
| WO | 90/00037 A1 | 1/1990 |
| WO | 92/01428 A1 | 2/1992 |
| WO | 92/06005 A1 | 4/1992 |
| WO | 93/01771 A1 | 2/1993 |
| WO | 95/08964 A2 | 4/1995 |
| WO | 95/15133 A1 | 6/1995 |
| WO | 95/20370 A1 | 8/1995 |
| WO | 95/21053 A1 | 8/1995 |
| WO | 95/26164 A1 | 10/1995 |
| WO | 96/39988 A2 | 12/1996 |
| WO | 96/40015 A1 | 12/1996 |
| WO | 97/20526 A1 | 6/1997 |
| WO | 97/23175 A1 | 7/1997 |
| WO | 97/25941 A1 | 7/1997 |
| WO | 97/25945 A1 | 7/1997 |
| WO | 97/37620 A1 | 10/1997 |
| WO | 97/39693 A1 | 10/1997 |
| WO | 98/17208 A2 | 4/1998 |
| WO | 98/17209 A2 | 4/1998 |
| WO | 98/55052 A1 | 12/1998 |
| WO | 98/56319 A1 | 12/1998 |
| WO | 98/56433 A1 | 12/1998 |
| WO | 99/09896 A1 | 3/1999 |
| WO | 99/09903 A1 | 3/1999 |
| WO | 99/27864 A2 | 6/1999 |
| WO | 99/29271 A1 | 6/1999 |
| WO | 99/32055 A1 | 7/1999 |
| WO | 99/38461 A2 | 8/1999 |
| WO | 99/38463 A2 | 8/1999 |
| WO | 99/56675 A1 | 11/1999 |
| WO | 99/63914 A1 | 12/1999 |
| WO | 00/07527 A1 | 2/2000 |
| WO | 00/07528 A1 | 2/2000 |
| WO | 00/25706 | 5/2000 |
| WO | 00/30568 A1 | 6/2000 |
| WO | 00/40177 A1 | 7/2000 |
| WO | 00/41654 A2 | 7/2000 |
| WO | 00/59412 A1 | 10/2000 |
| WO | 00/66044 A1 | 11/2000 |
| WO | 00/66045 a1 | 11/2000 |
| WO | 00/74607 A1 | 12/2000 |
| WO | 01/03615 A1 | 1/2001 |
| WO | 01/08611 A1 | 2/2001 |
| WO | 01/56497 A2 | 8/2001 |
| WO | 01/62190 A1 | 8/2001 |
| WO | 01/80785 A1 | 11/2001 |
| WO | 01/93742 A2 | 12/2001 |
| WO | 01/95837 A1 | 12/2001 |
| WO | 2004/000177 A1 | 12/2003 |
| WO | 2004/069106 A1 | 8/2004 |
| WO | 2005/007040 A1 | 1/2005 |
| WO | 2005/020861 A1 | 3/2005 |
| WO | 2006/138500 A2 | 12/2006 |
| WO | 07/98288 A2 | 8/2007 |
| WO | 2008/014258 A2 | 1/2008 |
| WO | 2008/082473 A1 | 7/2008 |
| WO | 2008/102174 A2 | 8/2008 |
| WO | 2008/124355 A1 | 10/2008 |
| WO | 2008/154326 A1 | 12/2008 |
| WO | 2009/064644 A1 | 5/2009 |
| WO | 2009/158319 A1 | 12/2009 |
| WO | 2010/054181 A1 | 5/2010 |
| WO | 2010/054208 A1 | 5/2010 |
| WO | 2012/088238 A2 | 6/2012 |

OTHER PUBLICATIONS

Plaintiffs' Supplemental Responses and Objections to Defendant Globus Medical Inc.'s Interrogatories Nos. 6-10 and Second Supplemental Responses and Objections to Interrogatory No. 5, United States District Court for the District of Delaware, Civil Action No. 11-cv-652-LPS, Sep. 1, 2012, 12 pages.

Plaintiffs' Responses and Objections to Defendant Globus Medical, Inc. 's First Set of Interrogatories (Nos. 1-11), United States District Court for the District of Delaware, Civil Action No. 1:11-cv-00652-LPS, Nov. 14, 2011, 18 pages.

PCT International Application No. PCT/US2009/063529: International Search Report and Written Opinion dated Apr. 14, 2010, 19 pages.

PCB Evolution Surgical Technique Guide 2010.

Parlov et al., "Anterior Lumbar Interbody Fusion with Threaded Fusion Cages and Autologous Grafts", Eur. Spine J., 1000, 9, 224-229.

Order, United States District Court District of Delaware, Civil Action No. 1: 11-cv-00652-LPS, May 7, 2013, 7 pages.

Order, United States District Court District of Delaware, Civil Action No. 1: 11-cv-00652-LPS, May 15, 2013, 4 pages.

Nasca, Newer Lumbar Interbody Fusion Techniques, 22(2) J. Surg. Ortho. Advances, 113-117, 2013.

Memorandum Opinion, United States District Court District of Delaware, Civil Action No. 1:11-cv-00652-LPS, May 7, 2013, 33 pages.

McAfee, Minimally Invasive Anterior Retroperitoneal Approach to the Lumbar Spine, 21 (13) Spine, 1476-1484, 1998.

Marcolongo et al., "Trends in Materials for Spine Surgery", Comprehensive Biomaterials, Biomaterials and Clinical Use, 6.610, Oct. 2011, 21 pages.

Malca, Cervical Interbody Xenografl with Plate Fixation, 21 (6) Spine, 685-690, Mar. 1996.

Lyu, Degradability of Polymers for Implantable Biomedical Devices, 10, Int. J. Mol. Sci., 4033-4065, 2009.

Lund, Interbody Cage Stabilisation in the Lumbar Spine, 80-8(2) J Bone Joint Surg., 351-359, Mar. 1998.

Kroppenstedt, Radiological Comparison of Instrumented Posterior Lumbar Interbody Fusion with One or Two Closed-Box Plasmapore Coated Titanium Cages, 33(19) Spine, 2083-2088, Sep. 2008.

Kozak, Anterior Lumbar Fusion Options, No. 300, Clin. Orth. Rel. Res., 45-51, 1994.

Khan, Chapter 2—Implantable Medical Devices, Focal Controlled Drug Delivery, Advances in Delivery Science and Technology, A.J. Domb and W. Khan (eds.) 2014.

(56) References Cited

OTHER PUBLICATIONS

Kastner, Advanced X-Ray Tomographic Methods for Quantitative Charecterisation of Carbon Fibre Reinforced Polymers, 4th Annual Intern. Symposium on NDT in Aerospace, 2012, 9 pages.
Jury Verdict Form, United States District Court District of Delaware, Civil Action No. 1: 11-cv-00652-LPS, Jun. 14, 2013, 20 pages.
Jury Trial Demanded, In the United States District Court for the District of Delaware, Case No. 1:11-cv-00652-LPS, filed Jul. 22, 2011,8 pages.
Jost, Compressive Strength of Interbody Cages in the Lumbar Spine: the Effect of Cage Shape, Posterior Instrumentation and Bone Density, 7 Eur. Spine J. 132-141, 1998.
Jonbergen et al., "Anterior CervicalInterbody fusion with a titanium box cage: Early radiological assessment of fusion and subsidence", The Spine Journal 5, Jul. 2005, 645-649.
Joint Claim Construction Brief, In the United States District Court for the District of Delaware, Civil Action No. 1: 11-cv-00652-LPS, Jun. 14, 2012, 97 pages.
Japanese Patent Application No. 2011-534928: Office Action dated Sep. 30, 2013, 11 pages.
Japanese Patent Application No. 2011-534926: Office Action dated Oct. 30, 2013, 7 pages.
International Search Report, dated Mar. 20, 2009, for PCT International Application No. PCT/US08/82473, filed Nov. 5, 2008.
International Search Report, dated Aug. 16, 2007 for International Application No. PCT/US2007/005098, filed Feb. 27, 2007, 5 pgs.
International Patent Application No. PCT /US2011/066421; International Search Report and Written Opinion dated Jun. 14, 2012, 31 pages.
International Patent Application No. PCT/CH2003/00089, International Search Report, dated Dec. 3, 2003, 3 pages.
Huttner, Spinal Stenosis & Posterior Lumbar Interbody Fusion, No. 193, Clinical Ortho Rel. Res. 103-114, Mar. 1985.
Gunatillake, Biodegradable Synthetic Polymers for Tissue Engineering, vol. 5, Eur. Cells Materials, 1-16, 2003.
Graham, Lateral Extracavitary Approach to the Thoracic and Thoracolumbar Spine, 20(7) Orthopedics, 605-610, Jul. 1997.
Germay, Resultats Cliniques de Ceramiques D'hydroxyapatite dans les arthrodeses Inter-somatiques du Rachis Cervical Par Voie Anterieure. Etude Retrospective a Propose de 67 cas. 13(3), Rachis 189-195, 2001 (w/Translation).
Fuentes, Les Complications de la Chirurgie Par Voie Anterieure du Rachis Cervical, 8(1) Rachis 3-14, 1996 (w/Translation).
Fowler, Complications Associated with Harvesting Autogenous Iliac Bone Graft, 24(12) Am. J. Ortho. 895-904, Dec. 1995.
Fassio, Use of Cervical Plate-Cage PCB and Results for Anterior Fusion in Cervical Disk Syndrome, 15(6) Rachis 355-361, Dec. 2003 Translation.
Expert Report of Richard J. Gering, Ph.D., CLP in the United States District Court for the District of Delaware, Civil Action No. 1: 11-cv-00652-LPS, Dec. 14, 2012, 39 pages.
Expert Report of Paul Ducheyne, PH.D. Concerning Patent Validity, United States District Court District of Delaware, Civil Action No. 1 :11-cv-00652-LPS,Dec. 13, 2012, 155pages.
Expert Report of John F. Hall, M.D., United States District Court for the District of Delaware,Civil Action No. 1 :11-cv-00652-LPS, Dec. 14, 2012, 27 pages.
Expert Report of Dr. Domagoj Carle Regarding the Invalidity of U.S. Pat. No. 7,846,207, U.S. Pat. No. 7,862,616 and U.S. Pat. No. 7,875,076, In the United States District Court for the District of Delaware, Civil Action No. 1:11-cv-00652-LPS, Nov. 5, 2012,149 pages.
Enker, Interbody Fusion and Instrumentation, No. 300 Clin. Orth. Rel. Res. 90-101, Mar. 1994.
Dickman, Internal Fixation and Fusion of the Lumbar Spine Using Threaded Interbody Cages, 13(3) Barrow Quarterly (1997); http://www.thebarrow.org/Education_And_Resources/Barrow_Quarterly/204837.

Dereymaeker, Nouvelle Cure neuro-Chirurgicale de discopathies Cervicales, 2 Neurochimrgie 226-234; 1956 (w/Translation).
DePuy Motech Surgical Titanium Mesh Brochure; 1998, 13 pages.
Delecrin, Morbidite du Prelevement de Greffons osseuz au Niveau des Creh'.:S Iliaques dans la Chirurgie Du Rachis; Justification du recours aux substituts osseuz, 13(3) Rachis 167-174, 2001 (w/Translation).
Dabrowski, Highly Porous Titanium Scaffolds for Orthopaedic Applications, J. Biomed Mater. Res. B. Appl. Biomat. Oct. 1995(1):53-61,2010.
Cloward, The Anterior Approach for Removal of Ruptured Cervical Disks, vol. 15, J. Neuro. 302-617, 1958.
Cloward, Gas—Sterilized Cadaver Bone Graffts for spinal Fusion Operation , 5(1) Spine Jan./Feb. 4-10, 1980.
Chadwick et al., "Radiolucent Structural Materials for Medical Application", www.mddionline.com/print/238 Jun. 2001, accessed Jul. 31, 2012, 9 pages.
Younger, Morbidity at Bone Graft Donor Sites, 3(3) J. Orth. Trauma, 192-195,1989.
Written Opinion, dated Mar. 20, 2009, for PCT International Application No. PCT/US08/82473, filed Nov. 5, 2008.
Wilson, Anterior Cervical Discectomy without Bone Graft, 47(4) J. Neurosurg. 551-555, Oct. 1977.
Whitesides, Lateral Approach to the Upper Cervical Spine for Anterior Fusion, vol. 59, South Med J, 879-883, Aug. 1966.
White, Relief of Pain by 1973 Anterior Cervical-Spine Fusion for Spondylosis, 55-A(3) J. Bone Joint Surg. 525-534, Apr. 1973.
Weiner, Spinde Update Lumbar Interbody Cages, 23(5) Spine, 634-640, Mar. 1998.
Watters, Anterior Cervical Discectomy with and without Fusion, 19(20) Spine 2343-2347 Oct. 1994.
Wang, Increased Fusion Rates with Cervical Plating for Two-Level Anterior Cervical Discectomy and Fusion, 25(1) Spine 41-45, Jan. 2000.
Wang, Determination of Cortical Bone Porosity and Pore Size Distribution using a Low Field Pulsed NMR Approach, J. Orthop Res., Mar. 21 (2):312-9 Mar. 2003.
Verbiest H., La Chirurgie Anterieure et Laterale du Rachis Cervical,16(S2) Neurochirurgie 1-212; 1970 (w/Translation).
U.S. Appl. No. 11/199,599: Preliminary Amendment, dated Jan. 9, 2008, 11 pages.
U.S. Appl. No. 11/199,599: Non-Final Rejection, dated Apr. 1, 2009, 20 pages.
U.S. Appl. No. 11/199,599: Interview Summary included Draft Amendments, dated Sep. 24, 2009,
U.S. Appl. No. 11/199,599: Final Rejection, dated Dec. 24, 2009, 21 pages.
U.S. Appl. No. 11/199,599: Appeal Brief, dated Apr. 15, 2010, 51 pages.
U.S. Appl. No. 11/199,599: Amendment/Request for Reconsideration after Non-Final Rejection, dated Sep. 29, 2009, 30 pages.
U.S. Provisional Application filed on Nov. 16, 2007 by Thomas Kueenzi et al. Entitled Low profile intervertebral implant., U.S. Appl. No. 60/988,661.
U.S Provisional Application Filed on Jan. 15, 1998 by David J. Urbahns et, al Entitled Insertion Instruments and Method for Delivering a Vertebral Body Spacer., U.S. Appl. No. 60/071,527.
U.S Provisional Application filed on Dec. 19, 1997, by David J. Urbahns et, al Entitled Insertion Instruments and Method for Delivering a Vertebral Body Spacer., U.S. Appl. No. 60/068,205.
U.S Provisional Application filed on Sep. 16, 2011, by Jillian Zaveloff et al. Entitled Multi-Piece Intervertebral Implants., U.S. Appl. No. 61/535,726.
Trial Transcript, United States District Court District of Delaware, Civil Action No. 1:11-cv-00652-LPS, Jun. 7, 2013, 97 pages.
Trial Transcript, United States District Court District of Delaware, Civil Action No. 1:11-cv-00652-LPS, Jun. 6, 2013, 80 pages.
Trial Transcript, United States District Court District of Delaware, Civil Action No. 1:11-cv-00652-LPS, Jun. 5, 2013, 99 pages.
Trial Transcript, United States District Court District of Delaware, Civil Action No. 1:11-cv-00652-LPS, Jun. 4, 2013, 110 pages.
Trial Transcript, United States District Court District of Delaware, Civil Action No. 1:11-cv-00652-LPS, Jun. 3, 2013, 98 pages.

(56) References Cited

OTHER PUBLICATIONS

Trial Transcript, United States District Court District of Delaware, Civil Action No. 1: 11-cv-00652-LPS, Jun. 14, 2013, 26 pages.
Trial Transcript, United States District Court District of Delaware, Civil Action No. 1: 11-cv-00652-LPS, Jun. 13, 2013, 94 pages.
Trial Transcript, United States District Court District of Delaware, Civil Action No. 1: 11-cv-00652-LPS, Jun. 12, 2013, 75 pages.
Trial Transcript, United States District Court District of Delaware, Civil Action No. 1: 11-cv-00652-LPS, Jun. 11, 2013, 98 pages.
Trial Transcript, United States District Court District of Delaware, Civil Action No. 1: 11-cv-00652-LPS, Jun. 10, 2013, 114 pages.
Tan, A Modified Technique of Anterior Lumbar Fusion with Femoral Cortical Allograft, 5(3) J. Ortho. Surg. Tech., 83-93, 1990.
Tamariz, Biodegradation of Medical Purpose Polymeric Materials and Their Impact on Biocompatibility, Chapter 1, Intech-bio degradation Life of Science, 2013; 28 pages.
Takahama, A New Improved Biodegradable Tracheal Prosthesis Using Hydroxy Apatite and Barbon Fiber 35(3) ASAIO Trans, 291-293, Jul.-Sep. 1989.
Synthes Spine, "Zero-P Instruments and Implants. Zero-Profile Anterior Cervical Interbody Fusion (ACIF) device", Technique Guide dated 2008, pp. 2-32, Published by Synthes Spine (USA).
Synthes Spine, "SynFix-LR System, Instruments and Implants for Stand-Alone Anterior Lumbar Interbody Fusion ALIF)", Technique Guide dated 2008, pp. 2-40, Published by Synthes Spine (USA).
Synthes Spine, "CorticoCancellous ACF Spacer. An allograft space or anterior fusion of the cervical spine," brochure, Musculoskeletal Transplant Foundationm, 2003, 6 pages.
Synthes Spine Cervical Stand-Alone Devices Presentation Brochure; 2010, 40 pages.
Synthes History and Evolution of LBIF Brochure; Nov. 2015, 30 pages.
Spruit et al., "The in Vitro Stabilizing Effect of Polyetheretherketone Cages Versus a Titanium Cage of similar design for anterior lumbar interbody fusion", Eur. Spine J., Aug. 2005, 14 752-758.
Sonntag, Controversy in Spine Care, Is Fusion Necessary Arter Anterior Cervical Discectomy 21(9) Spine, 1111-1113, May 1996.
Second Expert Report of Wilson C. Hayes, Ph.D., United States District Court for the District of Delaware, Civil Action No. 1: 11-cv-00652-LPS, Dec. 14, 2012, 22 pages.
Scholz et al., "A New Stand-Alone Cervical Anterior Interbody Fusion Device", Spine, Jan. 2009, 34(2), 6 pages.
Schleicher et al., "Biomechanical Comparison of Two Different Concepts for Stand-alone anterior lumbar interbody fusion", Eur. Spine J., Sep. 2008, 17, 1757-1765.
Samandouras, A New Anterior Cervical Instrumentation System Combinin an Intradiscal Cage with an Integrated plate, 26(10) Spine, 1188-1192, 2001.
Russian Patent Application No. 2011-1122797: Decision to Grant dated Oct. 9, 2013, 20 pages.
Reply Report of Dr. Domagoj Carle Regarding the Invalidity of U.S. Pat. No. 7,846,207, U.S. Pat. No. 7,862,616 and U.S. Pat. No. 7,875,076, in the United States District Court for the District of Delaware, Civil Action No. 1:11-cv-00652-LPS, Jan. 4, 2013, 81 pages.
Redacted version of "Plaintiff's Reply Brief in Support of Plaintiff's Motion for Summary Judgment of No Anticipation by the Kozak and Michelson References", Mar. 21, 2013, 11 pages.
Redacted version of "Opening Brief in Support of Plaintiffs' Motion for Summary Judgment of No Anticipation by the Kozak and Michelson References", United States District Court District of Delaware, Civil Action No. 1: 11-cv-00652-LPS, Feb. 13, 2013, 66 pages.
Redacted version of "Defendant Globus Medical, Inc.'s Answering Brief in Opposition to Plaintiff's Motion for Summary Judgment of No Anticipation by the Kozak and Michelson References", Mar. 12, 2013, 233 pages.
Porex Website, http://www.porex.com/technologies/materials/porous-plastics, Porous Elastic Materials, accessed Aug. 21, 2015, 2 pages.
Carbon Fiber Composite Ramps for Lumbar Interbody Fusion; Apr. 1997, 2 pages.
Bray, InterPlate Vertebral Body Replacement; website accessed May 4, 2017; http://rsbspine.com/Products.aspx, 2 pages.
Bray, "InterPlate Spine Fusion Device: Subsidence Control Without Stress Shielding", Orthopaedic Product News, Sep./Oct. 2006, pp. 22-25.
Brantigan, Pseudarthrosis Rate After Allograft Posterior Lumbar Interbody Fusion with Pedicle Screw and Plate Fixation , 19(11) Spine 1270-1280, Jun. 1994.
Brantigan, Intervertebral Fusion, Chapter 27, Posterior Lumbar Interbody Fusion Using the Lumbar Interbody Fusion Cage, 437-466, 2006.
Brantigan, Interbody Lumbar Fusion Using a Carbon Fiber Cage Implant Versus Allograft Bone, 19(13) Spine 1436-1444, 1994.
Brantigan, Compression Strength of Donor Bone for Posterior Lumbar Interbody Fusion, 18(9) Spine 1213-1221,1993.
Brantigan, A Carbon Fiber Implant to Aid Interbody Lumbar Fusion, 16(6S) Spine S277-S282, Jul. 1991.
Brantigan 1/F Cage for PLIF Surgical Technique Guide; Apr. 1991, 22 pages.
Benezech, L'arthrodese Cervicale Par Voie Anterieure a L'Aide de Plaque-Cage P.C.B., 9(1) Rach is 1, 47, 1997 (w/Translation).
Banward, Iliac Crest Bone Graft Harvest Donor Site Morbidity, 20 (9) Spine 1055-1060, May 1995.
Bailey, Stabilzation of the Cervical Spine by Anterior Fusion, 42-A(4), J. Bone Joint Surg., 565-594, Jun. 1960.
Appendix 3 to Joint Claim Construction Brief,Â—Exhibits A-C, In the United States District Court for the District of Delaware Civil Action No. 1: 11-cv-00652-LPS, Jun. 8, 2012, 38 pages.
Appendix 2 to Joint Claim Construction Brief,Â—Globus' Exhibits A-F, In the United States District Court for the District of Delaware Civil Action No. 1 :11-cv-00652-LPS, Jun. 8, 2012, 146 pages.
Appendix 1 to Joint Claim Construction Brief,Â—Synthes' Exhibits A-9, In the United States District Court for the District of Delaware Civil Action No. 1 :11-cv-00652-LPS, Jun. 8, 2012, 192 paqes.
Al-Sanabani, Application of Calcium Phosphate Materials in Dentistry, vol. 2013, Int. J. Biomaterials, 1-12, 2013.
AcroMed Carbon Fiber Interbody Fusion Devices; Jan. 1998, 8 pages.

* cited by examiner

INTERVERTEBRAL IMPLANT

CROSS REFERENCE TO RELATED APPLICATIONS

This application is a continuation of U.S. patent application Ser. No. 13/284,747, filed Oct. 28, 2011, which is a continuation of U.S. patent application Ser. No. 13/012,626, filed Jan. 24, 2011, which is a continuation of U.S. patent application Ser. No. 12/574,222, filed Oct. 6, 2009, now U.S. Pat. No. 7,875,076, issued Jan. 25, 2011, which is a continuation of U.S. patent application Ser. No. 11/751,757, filed May 22, 2007, now U.S. Pat. No. 7,618,456, issued Nov. 17, 2009, which is a continuation of U.S. patent application Ser. No. 10/923,534, filed Aug. 19, 2004, now U.S. Pat. No. 7,232,464, issued Jun. 19, 2007, which is a continuation of International Application No. PCT/CH02/00099, filed Feb. 19, 2002. The entire contents of each of the applications identified above are expressly incorporated herein by reference thereto.

TECHNICAL FIELD

The present invention relates to an intervertebral implant.

BACKGROUND

Such an intervertebral implant is known from the British patent document 2,207,607 A which discloses a horseshoe implant structure having a plurality of cylindrical holes. These holes are fitted with inner, smooth surfaces and comprise only one stop for the heads of the bone screws to be inserted into them. This design incurs the drawback that the inserted affixation screws may be anchored into the bone only by their shanks, a rigid connection with the horseshoe shaped intervertebral implant being lacking. As soon as the anchoring of the bone screw in the bone is weakened, the intervertebral implant becomes displaceable relative to the screw and the bone screws may then migrate while endangering the blood vessels. Moreover the loosening of the intervertebral implant may entail pseudoarthrosis.

The above cited state of the art is intended merely to elucidate the background of the present invention but it does imply that the cited state of the art had actually been made public or was publicly known at the time of this application or at the time of its priority.

SUMMARY

The objective of the present invention is palliation. This invention creates an intervertebral implant which is able to rigidly connect to bone affixation means in a manner that even in the event of bone structure weakening, loosening between the intervertebral implant and the bone affixation means shall be precluded.

The above problem is solved in the present invention by an intervertebral implant exhibiting the features of claim 1.

The advantages offered by the present invention substantially are attained by the rigid, that is by the firm connection between the intervertebral implant and the longitudinal affixing elements. Basically two different embodiment modes are available to attain said rigid connection.

In a first embodiment mode, at least one of the boreholes shall be internally threaded. In this case a matching bone screw fitted with a thread head may be rigidly screwed into the implant.

As regards a second embodiment mode, a front plate is mounted at the front surface of the three dimensional (3D) implant structure so as to be configured vertically to the horizontal center plane of the intervertebral implant, said boreholes passing through said front plate and receiving the anchored longitudinal affixation elements. Compared to the state of the art of a two-part implant, wherein a front plate is implanted in a separate operational step, the above design of the present invention offers the advantage that the intervertebral implant shall be implanted in a single step and hence in a simple and quicker manner. The invention offers a further advantage in that the intervertebral implant shall be affixed as frontally to the vertebra as possible, namely at a place where good bone material may be expected to be. As a result anterior displacement is restricted without thereby incurring greater danger to the surrounding structures than when using a state of the art intervertebral implant. The load still is being borne by the compressed vertebral implant, not by the front plate or the affixation screws.

In yet another embodiment mode of the present invention, the front plate is displaceably configured in the 3D implant structure in order that it may move vertically relative to this 3D implant structure. "Stress shielding" is attained in this manner (namely protection from or neutralization of mechanical stresses), and as a result the end plates may gradually match the intervertebral implant during the healing process.

As regards a further embodiment, the front plate is made of a material different from that of the 3D implant structure.

As regards a further embodiment of the present invention, at least one borehole tapers conically towards its underside and as a result a bone screw fitted with a matching conical head may be rigidly anchored in said borehole. Preferably the conical borehole exhibits a cone angle smaller than the resultant angle of friction. Appropriately the borehole's conicity shall be 1:3.75 to 1:20, preferably 1:5 to 1:15.

As regards a further embodiment mode of the present invention, the intervertebral implant side faces shall all be substantially convex.

Appropriately the intervertebral implant's top and/or undersides are not planar but convex. In this manner better matching to the end plates of the adjacent vertebras may be attained.

The boreholes preferably shall not pass through the left and right intervertebral implant side faces. Preferably again no borehole shall run through the front surface.

As regards a further preferred embodiment mode of the present invention, at least two boreholes shall be mutually parallel. This features facilitates inserting the vertebral implant during implantation.

As regards another preferred embodiment mode of the present invention, at least two boreholes shall run in mutually divergent manner as seen from the front side. As a result the bone screws shall move into a vertebral region offering better bone quality than found at the vertebra's center. Appropriately the borehole axes subtend an angle of 25 degrees to 70 degrees, preferably 35 degrees to 55 degrees with the horizontal center plane. This feature offers improved access for screw insertion.

As regards a further embodiment mode of the present invention, the boreholes shall not cross the horizontal center plane.

Depending on circumstance, two, three, four or even more longitudinal affixation elements may rigidly connected to the intervertebral implant; appropriately at least one affixation element shall pass through the top side and at least one affixation element shall pass through the intervertebral implant side.

Preferably the longitudinal affixation elements shall be bone screws comprising a head and a shank, said head preferably being fitted with an external thread that matches the inner thread of the intervertebral implant's borehole. As regards a second appropriate connection, preferably a bone screw shall be used of which the head tapers conically in the direction of the shank, the head's conicity corresponding to that of the intervertebral implant's borehole.

Regarding a further embodiment mode, at least two longitudinal affixation elements pass through the top side and at least two longitudinal affixation elements pass through the underside. In this manner the intervertebral implant is optimally anchored into the adjacent vertebras.

Preferably the screw-shaped longitudinal affixation elements exhibit a self-boring and self tapping external thread. The longitudinal affixation elements also may be designed as unthreaded cylindrical pins fitted with a boring tip, preferably in the form of a trocar.

In another embodiment variation, the longitudinal affixation elements are spiral springs; lastly said longitudinal affixation elements also may be designed as single or multi-wing spiral blades.

In a further embodiment mode of the present invention, the longitudinal affixation element tip may be anchored in the structure of the intervertebral implant, as a result of which the head of the longitudinal affixation element may be anchored in the adjacent vertebra.

In a further embodiment mode of the present invention, the longitudinal affixation element head exhibits a widened diameter; also a support disk is provided for said head to rest against the vertebra.

The intervertebral implant may be made of any physiologically compatible material, though appropriately the implant structure shall consist of a physiologically compatible plastic, preferably an unreinforced plastic. The advantage offered by the invention over the already known, fiber-reinforced plastics used in implantology is that no reinforcing fibers will be bared—an eventuality that would be clinically disadvantageous. Appropriately bone screws consisting of non-reinforced plastic of which the external threads exhibit load bevels of 11 degrees to 14 degrees, preferably 12 degrees to 13 degrees, may be used in such an implant structure. The relatively small slope of the load bevel implements high clamping forces, as a result of which radial elongation and danger of cracking of the plastic are reduced. Appropriately the bone screws' external thread exhibits the bones at an angular pitch of 6 degrees to 10 degrees, preferably 7 degrees to 9 degrees. This particular angular pitch produces thread self-locking and prevents the bone screw from loosening on its own.

The borehole may be in the form of a metal bush fitted with an inner thread for the purpose of improving anchoring the bone screw in the plastic implant structure. The intervertebral implant also may consist partly of plastic and, in the borehole zones, of metal. This design offers improved guidance and anchoring of the bone screw in the intervertebral implant.

As regards a further preferred embodiment mode, the inside borehole walls are smooth, the thread head of a metallic, longitudinal affixation element cutting or tapping into said smooth wall.

BRIEF DESCRIPTION OF THE DRAWINGS

The present invention and further embodiment modes of it are elucidated below in relation to the partly schematic representation of two illustrative embodiments.

DETAILED DESCRIPTION OF ILLUSTRATIVE EMBODIMENTS

Figure 1:
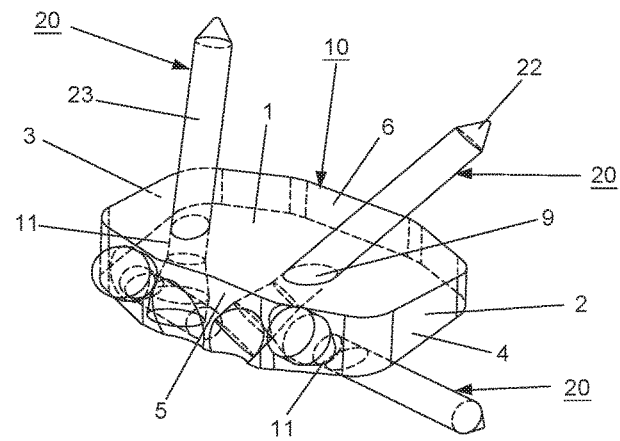
FIG. 1 is a perspective view including a partial section of the intervertebral implant with inserted bone screws.
Figure 2:
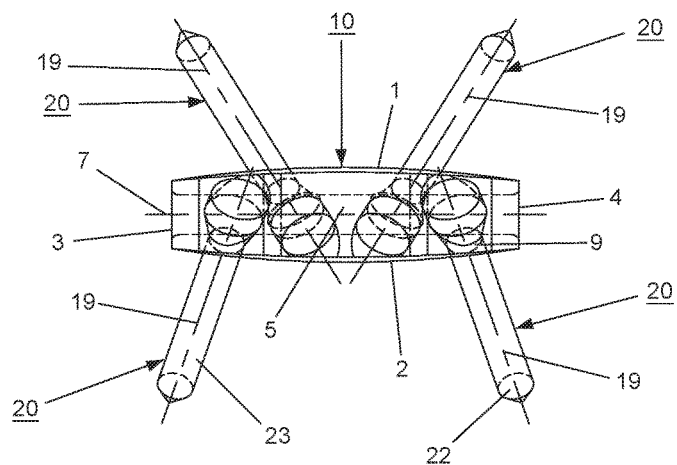
FIG. 2 is a front view of the intervertebral implant of FIG. 1.
Figure 3:
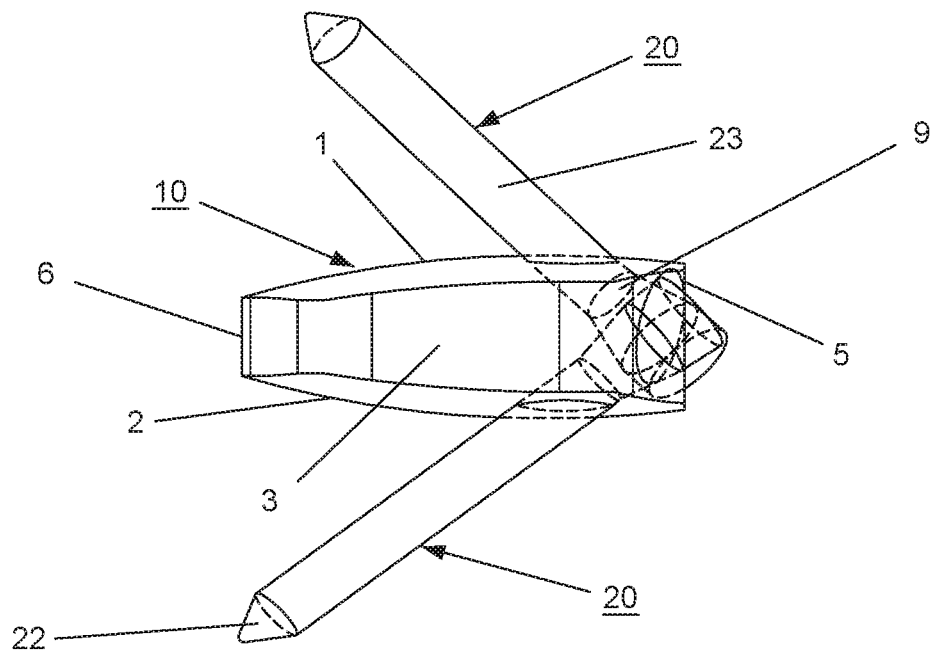
FIG. 3 is a side view of the intervertebral implant of FIG. 1.
Figure 4:
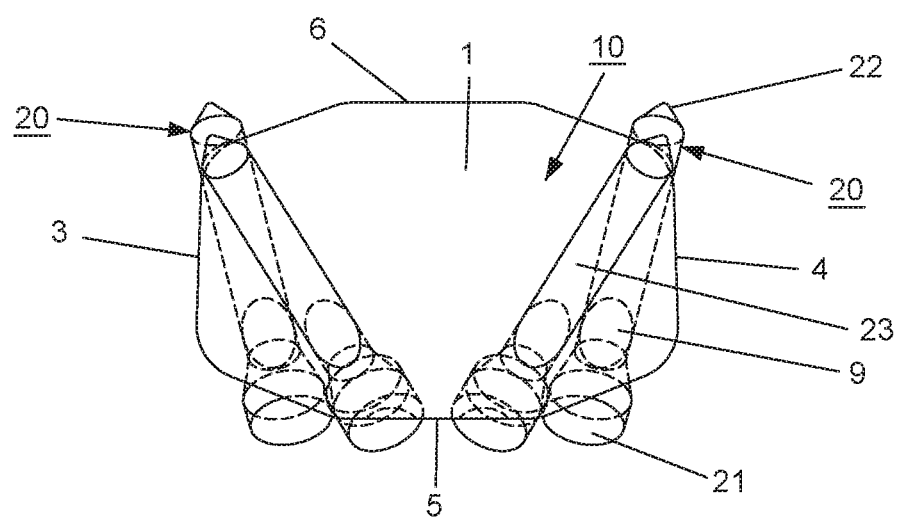
FIG. 4 is a top view of the intervertebral implant of FIG. 1.

The intervertebral implant of FIGS. 1 through 4 consists of a 3D structure 10 exhibiting both a convex top side 1 and a convex underside 2, the two sides each being designed to rest against the end plates of two adjacent vertebras. To attain improved anchoring, the top side 1 and the underside 2 may be topographically shaped and be fitted with grooves, ribs or teeth, or their surfaces may be merely roughened.

The 3D implant structure 10 moreover comprises a left side face 3 and a right side face 4, also a front face 5 and a rear face 6. The implant structure 10 also may be hollow and its outer surface may comprise perforations.

The implant structure 10 comprises a plurality of boreholes 9 passing through it and receiving longitudinal affixation elements 20. Preferably four such boreholes 9 shall be provided.

At least one of the boreholes 9 is designed in a way that the longitudinal affixation element 20 received therein may be rigidly connected to the intervertebral implant. The boreholes 9 are conical for that purpose.

Preferably the affixation elements 20 are bone screws having a head 21 and a tip 22. The head 21 conically tapers toward the shank 23, the conicity of the head 21 corresponding to the conicity of the borehole 9. Moreover the four boreholes 9 may be fitted with inner threads 11.

Figure 5:
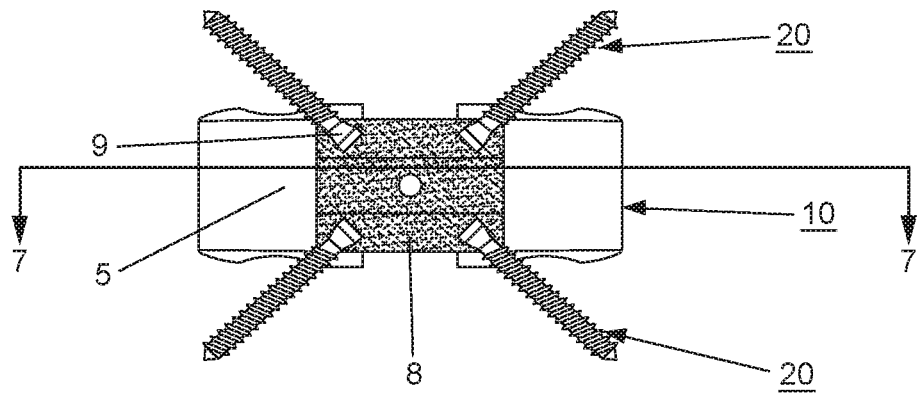
FIG. 5 is a front view of the intervertebral implant with a front insert, in partial section.
Figure 6:
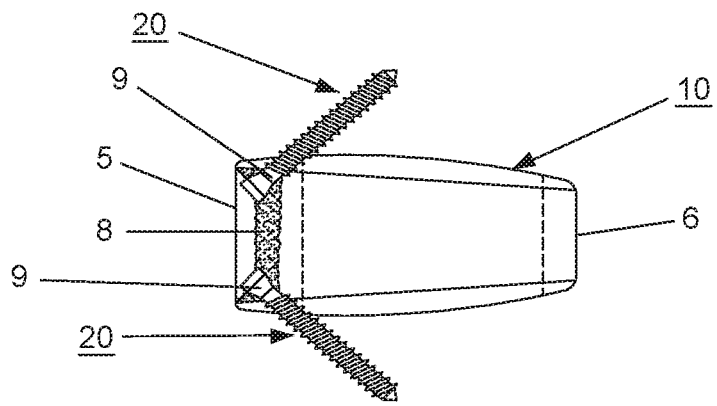
FIG. 6 is a vertical, longitudinal section of the intervertebral implant of FIG. 5.
Figure 7:
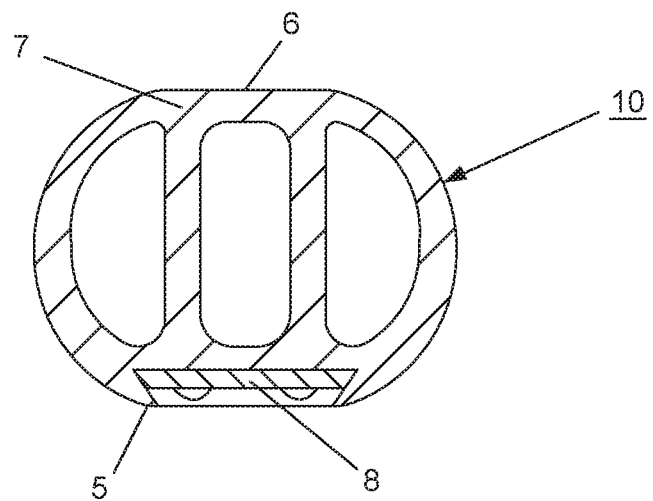
FIG. 7 is a horizontal cross-section of the intervertebral implant of FIG. 5.

As regards the embodiment variation shown in FIGS. 5 through 7, the 3D structure 10 is fitted at its front face 5 with a preferably metallic insert 8 into which the affixation elements 20 may be anchored. The insert 8 is mounted in vertically displaceable manner in the 3D structure 10.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention. Various other modifications may be made by those skilled in the art which will embody the principles of the invention and fall within the spirit and the scope thereof.

What is claimed:

1. An intervertebral implant configured to be inserted into a space between an endplate of an upper vertebral body and an endplate of a lower vertebral body, the intervertebral implant comprising:

an implant structure defining a front face a rear face, the front face spaced from the rear face in a first direction, a top side, and an underside opposite the top side in a second direction that is perpendicular to the first direction; and a plate including a front plate surface and a rear plate surface that is opposite the front plate surface, the plate further including a hole with an opening defined by the front plate surface, the hole being configured to receive a bone screw to secure the intervertebral implant to one of the upper vertebral body and the lower vertebral body, the plate configured to be coupled to the implant structure such that 1) the rear plate surface faces the front face of the implant structure, 2) an entirety of the opening is positioned between the top side and the underside with respect to the second direction, 3) the plate is movable relative to the implant structure along the second direction while interference between the implant structure and the plate restricts movement of the plate away from the implant structure in the first direction, wherein the rear face of the implant structure defines a rearmost surface of the intervertebral implant.

2. The intervertebral implant of claim 1, wherein the plate includes an upper plate surface and a lower plate surface opposite the upper plate surface in the second direction when the plate is coupled to the implant structure, the plate defines a maximum plate height measured from the upper plate surface to the lower plate surface along the second direction, the implant structure defines a maximum implant structure height measured from the top side to the underside along the second direction, and the maximum implant structure height is greater than the maximum plate height.

3. The intervertebral implant of claim 1, wherein the plate includes an upper plate surface and a lower plate surface opposite the upper plate surface in the second direction when the plate is coupled to the implant structure, the plate defines a minimum plate height measured from the upper plate surface to the lower plate surface along the second direction, the implant structure defines a maximum implant structure height measured from the top side to the underside along the second direction, and the maximum implant structure height is greater than the minimum plate height.

4. The intervertebral implant of claim 1, wherein the hole is a first hole, the opening is a first opening, the bone screw is a first bone screw, the plate includes a second hole with a second opening defined by the front plate surface, and the second hole is configured to receive a second bone screw to secure the intervertebral implant to the other of the upper vertebral body and the lower vertebral body.

5. The intervertebral implant of claim 4, wherein the plate is configured to be coupled to the implant structure such that the second opening is positioned between the top side and the underside with respect to the second direction.

6. The intervertebral implant of claim 1, wherein the plate is configured to be coupled to the implant structure such that a portion of the plate is positioned between a first portion of the implant structure and a second portion of the implant structure, and the portion of the plate is aligned with both the first portion of the implant structure and the second portion of the implant structure with respect to the first direction such that a straight line parallel to the first direction intersects each of the portion, the first portion, and the second portion.

7. The intervertebral implant of claim 1, wherein the plate defines a projection, the implant structure defines a recess, and the projection and the recess define corresponding shapes such that the recess is configured to receive the projection to couple the plate to the implant structure.

8. The intervertebral implant of claim 7, wherein the projection is a first projection, the recess is a first recess, the plate defines a second projection, the implant structure defines a second recess, and the second projection and the second recess define corresponding shapes such that the second recess is configured to receive the second projection to couple the plate to the implant structure.

9. The intervertebral implant of claim 8, wherein the first projection and the second projection are aligned with respect to a third direction that is perpendicular to both the first direction and the second direction.

10. The intervertebral implant of claim 1, further comprising an affixation element including a head and a shaft that extends from the head, the affixation element configured to be inserted through the hole and into the one of the upper vertebral body and the lower vertebral body.

11. The intervertebral implant of claim 10, wherein the plate is coupled to the implant structure such that 1) the rear plate surface faces the implant structure 2), the opening is positioned between the top side and the underside with respect to the second direction, and 3) the plate is movable relative to the implant structure along the second direction.

12. The intervertebral implant of claim 11, wherein the affixation element is inserted through the hole such that the head is positioned within the hole and between the top side and the underside with respect to the second direction.

13. An intervertebral implant configured to be inserted into a space between an endplate of an upper vertebral body and an endplate of a lower vertebral body, the intervertebral implant comprising:

an implant structure defining a front face, a rear face opposite the front face in a first direction, a top side, and an underside opposite the top side in a second direction that is perpendicular to the first direction; and a plate including a front plate surface, a rear plate surface that is opposite the front plate surface, an upper plate surface, and a lower plate surface opposite the upper plate surface in the second direction, the plate further including a hole with an opening defined by the front plate surface, the hole being configured to receive a fastener to secure the intervertebral implant to one of the upper vertebral body and the lower vertebral body, the plate configured to be coupled to the implant structure such that 1) the rear plate surface faces the front face of the implant structure, 2) the opening is positioned between the top side and the underside with respect to the second direction, and 3) the plate is movable relative to the implant structure along the second direction, wherein the lower plate surface is opposite the upper plate surface in the second direction when the plate is coupled to the implant structure, the plate defines a maximum plate height measured from the upper plate surface to the lower plate surface along the second direction, the implant structure defines a maximum implant structure height measured from the top side to the underside along the second direction, and the maximum implant structure height is greater than the maximum plate height, and wherein the rear face of the implant structure defines a rearmost surface of the intervertebral implant.

14. The intervertebral implant of claim 13, wherein the hole is a first hole, the opening is a first opening, the plate includes a second hole with a second opening defined by the front plate surface, the second hole is configured to receive a fastener to secure the intervertebral implant to the other of the upper vertebral body and the lower vertebral body, and the plate is configured to be coupled to the implant structure such that the second opening is positioned between the top side and the underside with respect to the second direction.

15. The intervertebral implant of claim 1, wherein interference between the implant structure and the plate structure further restricts movement of the plate along the implant structure in a third direction that is perpendicular to each of the first direction and the third direction.

* * * * *